United States Patent
Zamyatin et al.

(10) Patent No.: US 7,424,088 B2
(45) Date of Patent: Sep. 9, 2008

(54) IMAGE RECONSTRUCTION METHOD USING HILBERT TRANSFORM

(75) Inventors: Aleksandr A. Zamyatin, Buffalo Grove, IL (US); Katsuyuki Taguchi, Buffalo Grove, IL (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 259 days.

(21) Appl. No.: 10/951,650

(22) Filed: Sep. 29, 2004

(65) Prior Publication Data

US 2006/0067457 A1 Mar. 30, 2006

(51) Int. Cl.
*A61B 6/03* (2006.01)

(52) U.S. Cl. .............................. 378/4; 378/15; 378/901

(58) Field of Classification Search ...... 378/4, 378/15, 210, 901; *A61B 6/03*
See application file for complete search history.

(56) References Cited

U.S. PATENT DOCUMENTS 6,990,167 B2 * 1/2006 Chen .............................. 378/4

OTHER PUBLICATIONS

Chen, Guang-Hong, A new framework of image reconstruction from fan beam projections, Med. Phys. 30 (6), Jun. 2003, p. 1151-1161.*
Chen, Guang-Hong, An alternative derivation of Katsevich's cone-beam reconstruction formula, Med. Phys. 30 (12), Dec. 2003, p. 3217-3226.*
L. A. Feldkamp, et al., "Practical Cone-Beam Algorithm," Optical Society of America, vol. 1, No. 6, Jun. 1984, pp. 612-619.
A. Katsevich, et al., "Analysis of a Family of Exact Inversion Formulas for Cone Beam CT," Department of Mathematics, University of Central Florida, pp. 1-13.
Jed D. Pack, et al., "Investigation of Saddle Trajectories for Cardiac CT Imaging in Cone-Beam Geometry," Institute Physics Publishing, Physics in Medicine and Biology, vol. 49, 2004, pp. 2317-2336.
Hiroyuki Kudo, et al., "Exact and Approximate Algorithms for Helical Cone-Beam CT," Institute of Physics Publishing, Physics in Medicine and Biology, vol. 49, 2004, pp. 2913-2931.
Katsuyuki Taguchi, et al., "A New Weighting Scheme for Cone-Beam Helical CT to Reduce the Image Noise," Institute of Physics Publishing, Physics in Medicine and Biology, vol. 49, 2004, pp. 2351-2364.
Alexander Katsevich, "Improved Exact FBP Algorithm for Spiral CT," Department of Mathematics, University of Central Florida, pp. 1-19.
Alexander Zamyatin, "Analysis of Cone Beam Reconstruction in Computer Tomography," Department of Mathematics, University of Central Florida, Fall Term 2003, pp. i-viii and 1-69.

(Continued)

*Primary Examiner*—Edward J. Glick
*Assistant Examiner*—John M Corbett
(74) *Attorney, Agent, or Firm*—Oblon, Spivak, McClelland, Maier & Neustadt, P.C.

(57) ABSTRACT

A method of determining an image data value at a point of reconstruction in a computed tomography (CT) image of a scanned object, including obtaining projection data of the scanned object, filtering the obtained projection data with a one-dimensional ramp filter to generate ramp-filtered data, and applying a backprojection operator with inverse distance weighting to the ramp-filtered data to generate the image data value at the point of reconstruction in the CT image.

38 Claims, 17 Drawing Sheets

OTHER PUBLICATIONS

Michael D. Silver, "A Method for Including Redundant Data in Computed Tomography," Medical Physics, vol. 27, No. 4, Apr. 2000, pp. 773-774.

Ge Wang, et al., "A General Cone-Beam Reconstruction Algorithm," IEEE Transactions on Medical Imaging, vol. 12, No. 3, Sep. 1993, pp. 486-496.

Michael D. Silver, "Field-of-View Dependent Helical in Multi-Slice CT," Proceedings of SPIE vol. 4320, 2001, pp. 839-850.

Katsuyuki Taguchi, "Temporal Resolution and the Evaluation of Candidate Algorithms for Four-Dimensional CT," Medical Physics vol. 30, No. 4, Apr. 2003, pp. 640-650.

Alexander A. Zamyatin, et al., "Practical Hybrid Convolution Algorithm for Helical CT Reconstruction," supported by Toshiba Medical Systems, 2004, 5 pages.

Per-Erik Danielsson, et al., "The PI-Methods for Helical Cone-Beam Tomography," Physics in Medicine and Biology, Dec. 2001, pp. 1-14.

Carl R. Crawford, et al., "Computed Tomography Scanning with Simultaneous Patient Translation," Medical Physics, vol. 17, No. 6, Nov./Dec. 1990, pp. 967-982.

F. Noo, et al., "Image Reconstruction from Fan-Beam Projections on Less Than a Short Scan," Physics in Medicine and Biology, vol. 47, 2002, pp. 2525-2546.

H. Kudo, et al., "New Super-Short Scan Algorithms for Fan Beam and Cone-Beam Reconstruction," Conference Record of 2002 IEEE Nuclear Science Symposium and Medical Imaging Conference (paper M5-3, CD-ROM, ISBN 0-7803-7637-4), 5 pages.

A. Katsevich, "Analysis of an Exact Inversion Algorithm for Spiral Cone-Beam CT," Physics in Medicine and Biology. 2002, vol. 47, pp. 2583-2598, 14 pages.

A. Katsevich, "Theoretically Exact FBP-Type Inversion Algorithm for Spiral CT," The Sixth International Meeting on Fully Three-Dimensional Image Reconstruction in Radiology and Nuclear Medicine, Pacific Grove, CA, USA, Oct.-Nov. 2001, 4 pages.

* cited by examiner

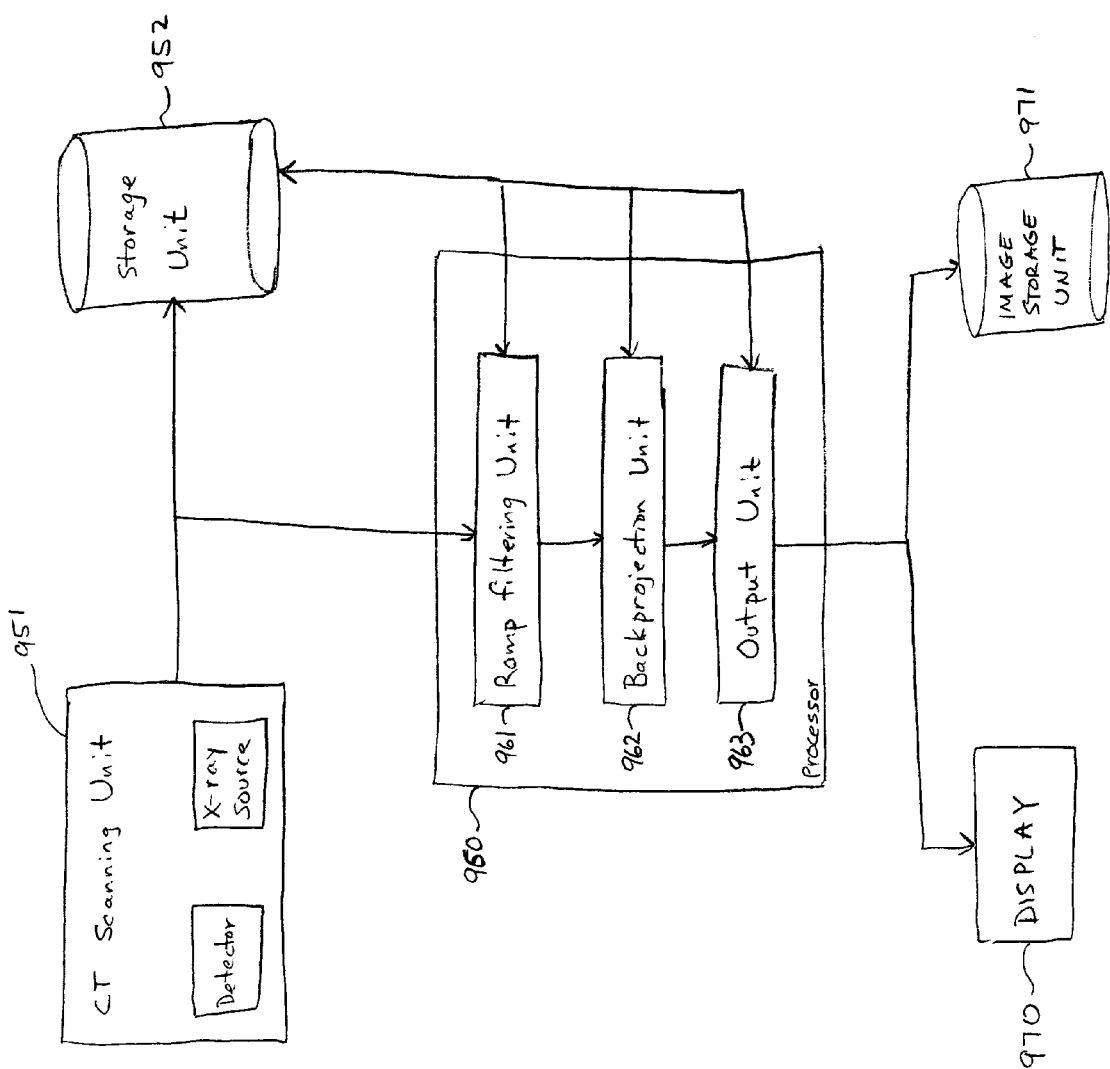

| Trajector | Det. geom | Projection range | Weight | Filtering direction |
|---|---|---|---|---|
| Fan beam data — Circular, Helical, Saddle | 1D | Super-short scan, Short scan, Full scan, Over scan, Flexible scan | Parker, MHS, OS, Noo | Horizontal |
| Cone beam data | 2D | | Parker, MHS, OS, Noo, Q3D, TW | Horizontal, Tangential, Rotated, Katsevich |

FIG. 11

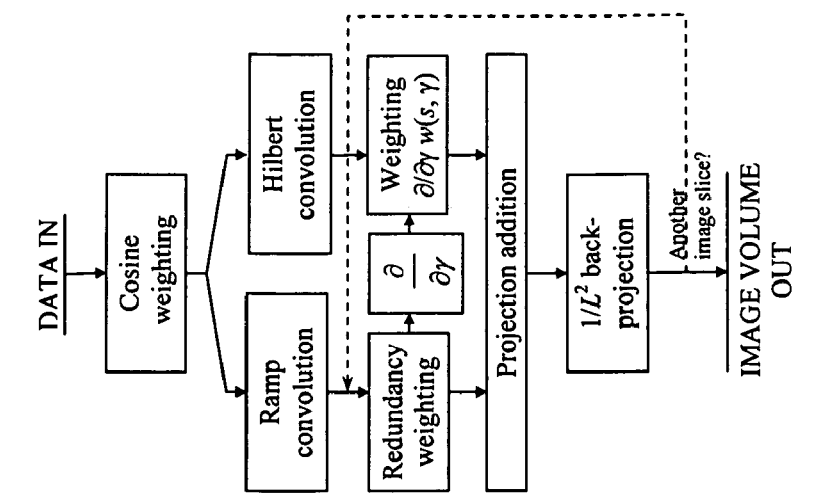
FIG. 13D
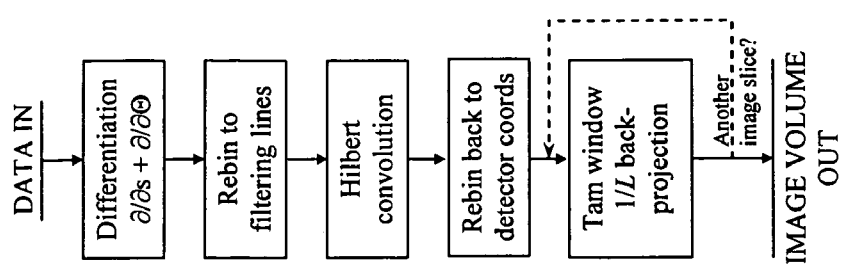
FIG. 13C
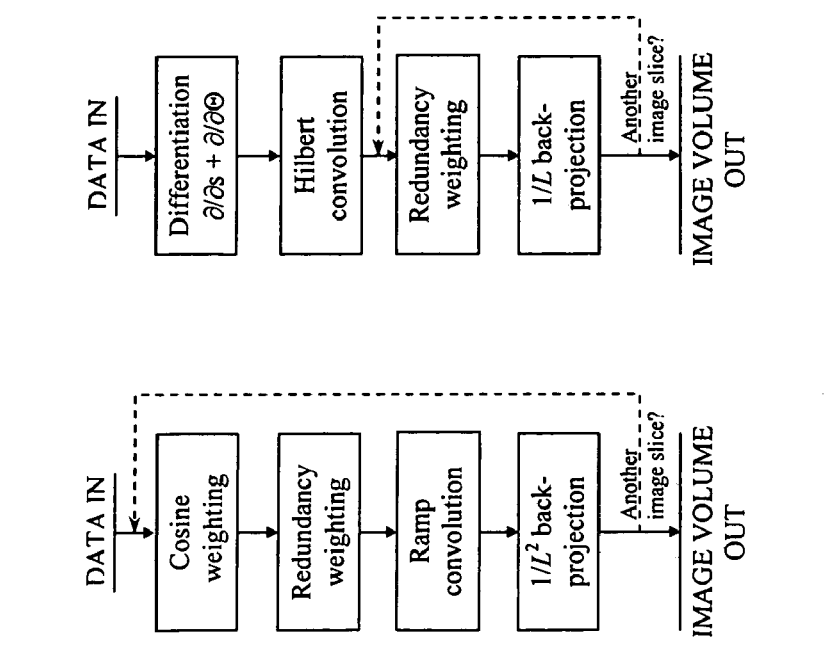
FIG. 13B
FIG. 13A

IMAGE RECONSTRUCTION METHOD USING HILBERT TRANSFORM

BACKGROUND OF THE INVENTION

Field of the Invention

The present invention relates generally to the reconstruction of medical images. More specifically, the present invention relates to a new method for improving the image quality and the efficiency of reconstruction by using hybrid filtering.

The present invention includes the use of various technologies referenced and described in the documents identified in the following LIST OF REFERENCES, which are cited throughout the specification by the corresponding reference number in brackets:

LIST OF REFERENCES

[1] C. R. Crawford and K. F. King, Computerized tomography scanning with simultaneous patient translation, *Med. Phys.*, 17, 967-982, 1990.

[2] P. E. Danielsson, P. Edholm, J. Eriksson and J. Seger, Towards exact 3D-econstruction for helical cone-beam scanning of long objects. A new detector arrangement and a new completeness condition, *Proc. on Fully 3D Image Reconstruction in Radiology and Nuclear Med.*, 141-144, 1997.

[3] L. A. Feldkamp, L. C. Davis, and J. W. Kress. Practical cone-beam algorithm, *J. Opt. Soc. Am*, vol. 1, pp. 612-619, 1984.

[4] G. T. Herman and A. Naparstek, Fast image reconstruction based on a Radon inversion formula appropriate for rapidly collected data, *SIAM J. Appl. Math.*, vol. 33, pp. 511-533, 1977.

[5] A. Katsevich, Theoretically Exact FBP-Type Inversion Algorithm for Spiral CT, *The Sixth International Meeting on Fully Three-Dimensional Image Reconstruction in Radiology and Nuclear Medicine*, Pacific Grove, Calif., USA, October-November 2001.

[6] A. Katsevich. An Improved Exact Filtered Backprojection Algorithm for Spiral Computed Tomography, *Advances in Applied Mathematics, V.* 32-4, pp. 625-825, May 2004.

[7] A. Katsevich, Analysis of an Exact Inversion Algorithm for Spiral Cone-Beam CT, *Physics in Medicine and Biology*, 2002, vol. 47, pp. 2583-2598.

[8] H. Kudo, F. Noo, M. Defrise and R. Clackdoyle, New super-short-scan reconstruction algorithms for fan-beam and cone-beam tomography, *IEEE NSS-MIC* 2002, M5-3.

[9] H. Kudo, F. Noo, M. Defrise, and T. Rodet, New Approximate Filtered Backprojection Algorithm for Helical Cone-Beam CT with Redundant Data, *IEEE NSS-MIC* 2003, M14-330.

[10] H. Kudo, T. Rodet, F. Noo, and M. Defrise, Exact and approximate algorithm for helical cone-beam ct with redundant data, *Phys. Med. Biol.* 49 (2004), 2525-2546.

[11] A. C. Kak and M. Slaney, Principles of computerized tomographic imaging, IEEE Press, New York, 1988.

[12] A. Katsevich and A. Zamyatin, Analysis of a family of exact inversion formulas for cone beam CT, submitted.

[13] A. V. Lakshminarayanan, Reconstruction from divergent ray data, *Tech. Rep.* 92, Dept. of Computer Science, SUNY at Buffalo, 1975.

[14] F. Natterer, The mathematics of computerized tomography, New York: Wiley, 1986.

[15] F. Noo, M. Defrise, R. Clackdoyle, H. Kudo, Image reconstruction from fan-beam projections on less then a short scan, *Phys. Med. Biol.*, 47, 2525-2546, 2002.

[16] D. L. Parker, Optimal short scan convolution reconstruction for fan-beam CT, *Med. Phys.* 9 (2), 1982, 254-257.

[17] J. D. Pack, F. Noo and H. Kudo, Investigation of saddle trajectories for cardiac CT imaging in cone-beam geometry, *Phys. Med. Biol.*, 49, No 11, 2317-2336, 2004.

[18] M. D. Silver, A method for including redundant data in computed tomography, *Med. Phys.*, 27, 773-774, 2000.

[19] M. D. Silver, K. Taguchi, and K. S. Han, Field-of-view dependent helical pitch in multi-slice CT *Proc. of SPIE Med. Imag Conf* 4320, 839-850, 2001.

[20] K. Taguchi, Temporal resolution and the evaluation of candidate algorithms for four-dimensional CT, *Med. Phys.*, 30 (4), 640-650, 2003.

[21] K. Taguchi, B. S. Chiang and M. D. Silver, A new weighting scheme for cone-beam helical CT to reduce the image noise, Phys. Med. Biol. 49, 2351-2364, 2004.

[22] K. C. Tam, S. Samarasekera, and F. Sauer, Exact cone-beam CT with a spiral scan, *Phys. Med. Biol.*, 43, 1015-1024, 1998.

[23] G. Wang, C. R. Crawford, W. A. Kalender, Multi-row-detector and cone-beam spiral/helical CT. *IEEE Trans. Med Imaging* 19:817-821, 2000

[24] G. Wang, T. H. Lin, P. Cheng and D. M. Shinozaki, A general cone-beam reconstruction algorithm, *IEEE Trans. Med. Imaging*, MI-12, 486-96, 1993.

[25] A. Zamyatin, Analysis of Cone Beam Reconstruction in Computer Tomography, PhD Dissertation, University of Central Florida, 2003.

DISCUSSION OF BACKGROUND

The quality and efficiency of a reconstructed image created by a computed tomography (CT) device are important to the overall effectiveness of the CT device. The algorithm used in reconstructing the image impacts quality and efficiency.

FIG. 1 illustrates an example of a possible source trajectory for a CT device, for which the reconstructed function $f(x)$, $x=(x_1, x_2)$ in 2D, and $x=(x_1, x_2, x_3)$ in 3D is obtained. The $x_3$ axis of FIG. 1 is identified with the z-axis. The helical trajectory, shown in FIG. 1, is given by the equation $a(t)=(R \cos t, R \sin t, tH/2\pi t)$, where H is called the helical pitch. Only a limited projection range is required for reconstruction of one image slice. Usually this projection range, denoted $\Lambda$, is centered at the image slice defined by $t_0=x_3 \cdot 2\pi/H$. The trajectory equations can be rewritten in terms of s, (e.g. $a(s)=(R \cos s, R \sin s, sH/2\pi)$, $s \in \Lambda$) by using $s=t-t_0$. Sometimes projection angle $\beta$ (or $\lambda$) is used instead of parameter s. Note that $\beta=s$ mod $2\pi$. L(s, x), illustrated in FIG. 1, denotes the horizontal distance from the point of reconstruction x to the focal spot a(s).

FIG. 1 illustrates the field of view (FOV) as a dashed circle. The FOV is the circle area containing the reconstructed object or patient. Usually the FOV is defined by its radius $r_{FOV}$. A typical value for the diameter of the FOV is 500 mm. The region of interest (ROI) can be a whole FOV or a part of an FOV.

Detector Geometry and Data Structure

Let $g(s, \Theta)$ represents the total attenuation (or line integral) along a ray from the source position a(s) in direction $\Theta$. This function represents the data acquired through the CT scan before reconstruction has taken place. As is illustrated by FIG. 2, $\gamma$ denotes a fan angle, and $\alpha$ denotes a cone angle. In the case of a fan-beam, $\Theta=\gamma$. In the case of a cone-beam, $\Theta=(\gamma, \alpha)$. Angle $\Theta$ can also be represented in reference to the detector. In reference to the detector, $\Theta_D=(u, v)$ (or $\Theta_D=u$ for fan-beam case), and hence $\Theta_D$ depends on detector geometry. In practice, cone-beam data is a function of detector coordinates $g(s, \Theta_D)=g(s, u, v)$, but some theoretical formulas treat it as a function of fan and cone angles $g(s, \Theta)=g(s, \gamma, \alpha)$, i.e. detector-free notation. Detector free notation is used here.

There are many detector types with different geometries: equi-angular, equi-spaced, non-equi-spaced, flat, cylindrical, spherical, tilted, rotated, PI-masked, etc. FIG. 2 illustrates an equi-angular cylindrical detector and FIG. 3 illustrates a flat equi-spaced collinear detector.

Convolution

For clarity, operator notation will be used. Each operator, convolution or backprojection, is defined in general, independently from its argument. Operators are formatted in bold italic to distinguish from functions. Relevant operators are defined as follows.

The Fourier transform is defined as $G(s, \omega))=FT[g(s, \gamma)]$, in which the Fourier transform is applied on the second variable $\gamma$.

The Hilbert filtering operator (H) is defined as $H[g(s, \gamma)]=g(s, \gamma)*h(\gamma)$ $H[g(s, \gamma)]=FT^{-1}[G(s,\omega)H(\omega))$ ], where $h(\gamma)=-1/(\pi\gamma)$ and $H(\omega)=i$ sign $\omega$.

The ramp filtering operator (Q) is defined as $Q[g(s, \gamma)]=g(s, \gamma)*q(\gamma)$ $Q[g(s, \gamma)]=FT^{-1}[G(s,\omega))Q(\omega))$ ], where $q(\gamma)=FT^{-1}[Q(\omega)]$ and $Q(\omega)=|\omega|$.

The modified Hilbert filtering operator ($H_m$) (modified meaning that the kernel is $h(\sin \gamma)$ rather than $h(\gamma)$) is defined as $H_m[g(s, \gamma)]=g(s, \gamma)*h(\sin \gamma)$.

The modified ramp filtering operator ($Q_m$) is defined as $Q_m[g(s, \gamma)] = g(s, \gamma)*q(\sin\gamma)$, where $q(\sin\gamma) = \left(\dfrac{\sin\gamma}{\gamma}\right)^2 q(\gamma)$ and $Qm(\omega) = FT[q(\sin\gamma)]$.

Finally, the modified Ramp filtering operator with DC shift ($Q_{m0}$) is defined as $Q_{m0}[g(s, \gamma)]=FT^{-1}[G(s, \omega)Qm(\omega))-G(s, \omega)\delta(\omega)]$ $Q_{m0}[g(s, \gamma)]=g(s, \gamma)*q(\sin \gamma)-G(s, \gamma)/2\pi$, where $\delta(\omega)$ is the delta-function, given by $FT[\delta]=1$.

Ramp filtering is traditionally used in filtered backprojection (FBP) algorithms. FBP is the main reconstruction method in computed tomography (CT). Compared to Hilbert filtering, it has the following advantages: (1) better resolution (sharper image) for the same noise level, and (2) more control over resolution to noise trade-off in reconstruction. The second advantage is very important for clinical applications. In the present invention, the major contribution to a reconstructed image comes from ramp-filtered data. Ramp-filtering preserves all high-frequency components of the image. Hilbert-filtering, which is a low-frequency correction, helps reducing cone-beam artifacts.

Backprojection

In general, the backprojection operator acts on data $g(s, \Theta))$, wherein the operator maps the data into image space. This is denoted by the following equation:

$$BPJ[g(s, \Theta)](x) = \dfrac{1}{4\pi}\int_\Lambda g(s, \Theta)\Big|_{\Theta=\Theta(s,x)} ds$$

Here $g(s, ")$ is first evaluated at $\Theta=\Theta(s, x)$, wherein $\Theta(s, x)$ is a ray from $a(s)$ that crosses x. Then the equation integrates all such rays along the source trajectory over the projection range $\Lambda$.

To find $\Theta(s, x)$ the following equations are used:

$$\gamma(s, x) = \arcsin\dfrac{x_1\sin s - x_2\cos s}{L(s, x)} \text{ and}$$

$$\alpha(s, x) = \arctan\dfrac{x_3 - z_{a(s)}}{L(s, x)},$$

where $z_{\alpha(s)}$ is the z-coordinate of $\alpha(s)$. Backprojection is usually applied to filtered data.

There are two methods for weighting the backprojection operator. The backprojection operator can be either weighted by the inverse of L or the inverse of $L^2$. These two methods are shown in the two following equations.

$$BPJ_L[g(s, \Theta)](x) = \dfrac{1}{4\pi}\int_\Lambda \dfrac{1}{L(s, x)} g(s, \Theta)\Big|_{\Theta=\Theta(s,x)} ds$$

$$BPJ_{L^2}[g(s, \Theta)](x) = \dfrac{1}{4\pi}\int_\Lambda \dfrac{R}{L^2(s, x)} g(s, \Theta)\Big|_{\Theta=\Theta(s,x)} ds$$

Compared to 1/L, a backprojection weight of $1/L^2$ results in worse noise and point-spread-function (PSF) uniformity throughout the image.

The backprojection range is denoted by $\Lambda$. Let the superscript in the BPJ operator notation denote the backprojection range as indicated below:

$$BPJ^\Lambda[g(s, \Theta)](x) = \dfrac{1}{2\pi}\int_\Lambda g(s, \Theta)\Big|_{\Theta=\Theta(s,x)} ds$$

FIGS. 4A-4E illustrate five different reconstruction ranges. FIG. 4A shows a full scan, FIG. 4B shows an over-scan, FIG. 4C shows a short scan, FIG. 4D shows a super-short scan and FIG. 4E shows a flexible range.

Redundancy Compensation Weighting

A weighting factor, $w(s, \gamma)$, may be used to correct for redundancy in the data. It is not necessary to scan over the entire region for fan-beam data. For fan-beam geometry, $g(s, \gamma)=g(s+\pi+2\gamma, -\gamma)$. For fan-beam data, a whole scan will result in each ray being counted twice. Thus, the data would need to be weighted by the function $w(s, \gamma)=\frac{1}{2}$. The 2D data sufficiency condition [14] is satisfied when any line crossing the FOV intersects the reconstruction segment at least once. The 2D data sufficiency condition is satisfied when the reconstruction range $\Lambda \geq \pi + 2 \arcsin (r_{FOV}/R)$. The set of projections that covers $\Lambda = \pi + 2 \arcsin (r_{FOV}/R)$ is referred to as a "minimum complete data set" [16] for fan-beam data. The following terminology has been adopted in the art and will be used here:

short-scan, or half-scan reconstruction: $\Lambda = \pi + 2\Gamma$, $\arcsin (r_{FOV}/R) \leq \Gamma < \pi/2$;

super-short-scan reconstruction: $\Lambda < \pi + 2 \arcsin (r_{FOV}/R)$;

full-scan reconstruction: $\Lambda = 2\pi$; and over-scan reconstruction: $\Lambda > 2\pi$.

Parker Weighting for Short Scan

From the relation $g(s, \gamma) = g(s + \pi + 2\gamma, -\gamma)$, where $-\gamma_m \leq \gamma \leq \gamma_m$, it can be seen that only a $\pi + 2\gamma_m$ reconstruction range is sufficient for exact fan-beam reconstruction and the data $g(s, \gamma)$, $0 < s < 2\gamma_m - 2\gamma$, is redundant with the data in the region $\pi - 2\gamma < s < \pi 2\gamma_m$. Here $\gamma_m = \arcsin (r_{FOV}/R)$ is the maximum fan angle allowed by the detector. Reference [16] suggests that in Parker weighting, the data of the minimal complete data set should be weighted in such a way that the discontinuity is as uniformly distributed as possible. Reference [16] proposed the following weighting function:

$$w_P(s, \gamma) + w_P(s + \pi + 2\gamma, -\gamma) = 1$$

$$w_P(s, \gamma) = \begin{cases} \sin^2\left(\frac{\pi}{4} \frac{s}{\gamma_m - \gamma}\right), & 0 \leq s \leq 2\gamma_m - 2\gamma \\ 1, & 2\gamma_m - 2\gamma \leq s \leq \pi - 2\gamma \\ \cos^2\left(\frac{\pi}{4} \frac{\pi + 2\gamma_m - s}{\gamma_m + \gamma}\right), & \pi - 2\gamma \leq s \leq \pi + 2\gamma_m \end{cases}$$

$\gamma_m = \arcsin (r_{FOV}/R)$ is the maximum fan angle allowed by the detector. The weight is zero if not defined, e.g., $w_P(s, \gamma) = 0$ if $s < 0$ or $s > \pi + 2\gamma_m$. Let the superscript P in the BPJ operator notation denote a backprojection range of $\pi + 2\gamma_m$:

$$BPJ^P[g(s, \Theta)](x) = \frac{1}{2\pi} \int_{-\pi/2 - \gamma_m}^{\pi/2 + \gamma_m} g(s, \Theta)\bigg|_{\Theta = \Theta(s,x)} ds.$$

Generalized Parker Weighting (MHS Weighting)

Parker weighting is a particularized case of MHS weighting. In MHS weighting, $\gamma_m$ should be at least $\arcsin (r_{FOV}/R)$. By virtually increasing $\gamma_m$, a larger reconstruction range can be obtained and this allows for better noise properties [18, 19]. By replacing the physical maximum fan angle $\gamma_m$ with the virtual maximum fan angle $\Gamma$ in the equation for $w_P(\beta, \gamma)$, the following equation is obtained:

$$w_{MHS}(\beta, \gamma) = \begin{cases} \sin^2\left(\frac{\pi}{4} \frac{\beta}{\Gamma - \gamma}\right), & 0 \leq \beta \leq 2\Gamma - 2\gamma \\ 1, & 2\Gamma - 2\gamma \leq \beta \leq \pi - 2\gamma \\ \sin^2\left(\frac{\pi}{4} \frac{\pi + 2\Gamma - \beta}{\Gamma + \gamma}\right), & \pi - 2\gamma \leq \beta \leq \pi + 2\Gamma \end{cases}$$

Let the superscript MHS in the BPJ operator notation denote a backprojection range of $\pi + 2\Gamma$:

$$BPJ^{MHS}[g(s, \Theta)](x) = \frac{1}{2\pi} \int_{-\pi/2 - \Gamma}^{\pi/2 + \Gamma} g(s, \Theta)\bigg|_{\Theta = \Theta(s,x)} ds, \text{ where}$$

$$\sin^{-1} \frac{r_{FOV}}{R} \leq \Gamma < \frac{\pi}{2}.$$

Over-Scan Weighting

Since $g(s, \gamma) = g(s + 2\pi, \gamma)$, over-scan weighting is used for the backprojection range $\Lambda = 2\pi n + \Delta$, where $n = 1, 2, \ldots, 0 < \Delta < 2\pi$. The weight function is given below.

$$w_{OS}(\beta) = \frac{1}{2n} \begin{cases} \sin^2\left(\frac{\pi}{2} \frac{\beta}{\Delta}\right), & 0 \leq \beta < \Delta \\ 1, & \Delta \leq \beta \leq 2\pi n \\ \cos^2\left(\frac{\pi}{2} \frac{\beta - 2\pi n}{\Delta}\right), & 2\pi n < \beta \leq 2\pi n + \Delta \end{cases}$$

In over-scan weighting, MHS weighting and Parker weighting, instead of trigonometric functions $\sin^2$ or $\cos^2$, a polynomial $3x^2 - 2x^3$ [1] or some other smooth function can be used Let the superscript OS in the BPJ operator notation denote a backprojection range of $2\pi n + \Delta$:

$$BPJ^{OS}[g(s, \Theta)](x) = \frac{1}{2\pi} \int_{-\pi n - \Delta/2}^{\pi n + \Delta/2} g(s, \Theta)\bigg|_{\Theta = \Theta(s,x)} ds.$$

Noo's Weighting

Noo's weighting has the advantage that it allows the use of an arbitrary reconstruction range $\Lambda = (s_0, s_1)$, where so and si are starting and ending points of the reconstruction segment. This weight can be used for ROI reconstruction with a reconstruction range less than half-scan. Such a reconstruction range is called a short scan. The weight function is given below:

$$w_N(s, \gamma) = \frac{c(s)}{\sum_{comp} c(s_{comp}, \gamma_{comp})}$$

For example, in a simple short scan case, $$\sum_{comp} c(s_{comp}, \gamma_{comp}) = c(s) + c(s + \pi + 2\gamma).$$

For an over-scan case:

$$\sum_{comp} c(s_{comp}, \gamma_{comp}) = c(s) + c(s + \pi + 2\gamma) + c(s + 2\pi)$$

The function $c(\beta)$ is given by:

$$c(\beta) = \begin{cases} \cos^2 \frac{\pi(s - s_0 - \Delta s)}{2\Delta s}, & s_0 \leq s \leq s_0 + \Delta s \\ 1, & s_0 + \Delta s \leq s \leq s_1 - \Delta s \\ \cos^2 \frac{\pi(s - s_1 + \Delta s)}{2\Delta s}, & s_1 - \Delta s \leq s \leq s_1 \end{cases}$$

where $\Delta s$ is the smoothing interval. Noo suggested taking $\Delta s = 10°$ [15]. Note that Noo's weighting, with large $\Delta s$ ($\approx 50°$), is equivalent to Parker weighting. Noo's weighting allows the using of an arbitrary backprojection range $\Lambda$ as shown in FIGS. 4A-4E [15].

Quasi Cone-Beam Weighting

Fan-beam weighting can be extended to cone-beam data [21]. Once a fan-beam weight $w(\beta, \gamma)$ is calculated, it is weighted as a function of the cone angle and normalized to obtain a quasi cone-beam weighting function $W_{Q3D}(\beta, \gamma, \alpha)$. This weight must be defined based on the validity (accuracy) of the data, which is represented by the validity weight $$w_{Val}(\alpha) = 1 - a(3x^2 - 2x^3), \text{ where}$$

$$x = \begin{cases} 0 & \text{if } |\alpha| \le \alpha_1 \\ (\alpha - \alpha_1)/(\alpha_2 - \alpha_1) & \text{if } \alpha_1 < |\alpha| \le \alpha_2 \text{ and} \\ 1 & \text{otherwise} \end{cases}$$

$$\alpha_1 = \tan^{-1}[t_1 D/(2R)]; \alpha_2 = \tan^{-1}[t_2 D/(2R)].$$

The two cone-angles ($\alpha_1$ and $\alpha_2$) define the turning points of the validity curve. The validity weight $w_{Val}(\alpha)$ is combined with a fan-beam weighting function $w(\beta, \gamma)$ and then normalized in order to compensate for redundant samples. The validity weight $w_{Val}(\alpha)$ can be arbitrary; however, it makes sense if the parameters $t_1$ and $t_2$ are chosen such that $w_{Val}(\alpha)$ assigns full weight to valid (measured) ray-sums, less weight to invalid (unmeasured) ray-sums and lets the transition be smooth. Therefore, the quasi cone-beam weighting function is:

$$w_{Q3D}(\beta, \gamma, \alpha) = w(\beta, \gamma) w_{Val}(\alpha) \bigg/ \sum_{comp} w(\beta_{comp}, \gamma_{comp}) w_{Val}(\alpha_{comp}),$$

where summation is performed over all complementary positions, such that $$\sum_{comp} w(\beta_{comp}, \gamma_{comp}) w_{Val}(\alpha_{comp}) = 1.$$

Tam Window Weighting

The Tam window is a part of the detector bounded by the upper and lower projections of the helix from the focal spot $a(s)$. FIG. 5 shows that a $\pi$ Tam window contains only non-redundant data and is complete [22, 2]. FIG. 5 shows the case of rH=1.0. Dashed lines represent boundaries of the physical detector when rH=1.25. Here rH=H/D, where D is the detector width. The weighting function for a $\pi$ Tam window is given by:

$$w_T(\gamma, v) = \begin{cases} 1, & -\dfrac{H(\pi - 2\gamma)}{4\pi\cos\gamma} < v < \dfrac{H(\pi + 2\gamma)}{4\pi\cos\gamma} \\ 0, & \text{otherwise} \end{cases}$$

The weighting function for a $3\pi$ Tam window is given by:

$$w_T(\gamma, v) = \begin{cases} 1/2, & -\dfrac{H(3\pi - 2\gamma)}{4\pi\cos\gamma} < v < \dfrac{H(3\pi + 2\gamma)}{4\pi\cos\gamma} \\ 0, & \text{otherwise} \end{cases}$$

Let the superscript $\pi$ in the BPJ operator notation denote backprojection for a $\pi$ Tam window only, and the superscript TW in the BPJ operator notation denote backprojection for a Tam window, $\pi$ or $3\pi$, depending on the helical pitch:

$$BPJ^{TW}[g(s, \Theta)](x) = \frac{1}{2\pi} \int w_T(\gamma, v) g(s, \Theta) \bigg|_{\Theta = \Theta(s, x)} ds.$$

Note that both Parker and Noo's weighting functions were originally introduced for fan-beam data and are cone-angle independent. Use of these weighting functions results in cone-beam artifacts. Tam window weighting provides 3D weighting and is shift-invariant or projection angle independent, i.e., the same weight is applied for each projection.

The advantages of Tam window weighting are: (1) true cone-beam weight, (2) shift-invariance, i.e., the weighting function $W_T(\gamma, v)$ is the same for all projections, independently of z-position, and (3) simplicity of implementation. The disadvantages of Tam window weighting are: (1) no redundant data is used (some part of the measured data is not used), (2) the Tam window is fixed (hence only two helical pitches are optimal, corresponding to $\pi$ and $3\pi$), and (3) different image pixels are reconstructed using different backprojection ranges, which leads to a less spatially uniform image.

In FIG. 6, the dashed lines represent the paths of two different image points along the detector as the source moves along the helix. Bold lines represent the data used in backprojection to reconstruct the points A and B. Thus, as can be seen from FIG. 6, the reconstruction of point A uses more data than the reconstruction of point B.

Extended Tam Window Weighting

A Tam window can be extended in the z-direction by using smoothing functions. The extended Tam window is illustrated in FIG. 7. An extended Tam window weighting may lose theoretical exactness, but it allows for better data usage. Let the superscript ETW in BPJ operator notation denote extended Tam window weighting:

$$BPJ^{ETW}[g(s, \Theta)](x) = \frac{1}{2\pi} \int w_{ET}(\gamma, v) g(s, \Theta) \bigg|_{\Theta = \Theta(s, x)} ds.$$

Direction of Filtering Lines

FIGS. 8A-8F illustrate different filtering lines. Originally, filtering was performed along detector rows, or segments (FIG. 8A). For a helical trajectory, filtering along the lines parallel to the tangent of the helix at the point of source position (tangential lines) helps to reduce cone-beam artifacts. Operators denoted by $H^{Tan}$ and $Q^{Tan}$ filter along tangential lines (FIG. 8B). In rotated filtering (FIG. 8C), the middle filtering line is tangential to the helix, and the top-most and the bottom-most filtering lines are horizontal (flat). Other filtering lines between them are gradually rotated to form a smooth family of lines. Operators denoted by $H^{Rot}$ and $Q^{Rot}$ filter along rotated lines. Exact algorithms [12] use Katsevich's families of filtering lines. Katsevich filtering lines can be seen in FIGS. 8D-8F, and filtering along Katsevich's family of curves is denoted $H^{Kat}$ and $Q^{Kat}$.

In actual implementation, if the detector rows are not parallel to the filtering direction, filtering requires rebinning from the detector grid to the filtering grid. Each rebinning involves interpolation, which results in a smoother image and possible loss of details. The use of $H^{Tan}$ and $Q^{Tan}$ operators (as well as others) allows for the reduction in cone-beam artifacts for the price of increased reconstruction time and reduced resolution.

Order of Weighting and Convolution

The order of performing weighting and convolution is very important in practice. Redundancy weight $w(s(x_3), \gamma)$ depends on the reconstructed slice z-position, $x_3$. If weighting has to be performed before convolution, i.e., filtering applies to weighted data subsets, then for each slice, all projections in the reconstruction range need to be re-weighted and re-convolved. If, on the other hand, weighting follows after convolution, then the data can be convolved only once for all image slices, and then each slice only needs to be re-weighted. Hence, in the latter case, the number of convolutions required for reconstruction is greatly reduced.

Reconstruction Algorithms

Ramp filtering is traditionally used in FBP algorithms that are used to reconstruct medical images. The original FBP algorithm for fan-beam data has the following form:

$$[FBP]f(x) = \frac{1}{4\pi}\int_{-\pi}^{\pi}\frac{1}{L^2(s,x)}Q_m[g(s,\gamma)\cos(\gamma)]_{\gamma=\gamma(s,x)}ds,$$

which in operator notation becomes:

$f(x)=BPJ_{L^2}[Q_m[g(s,\gamma)\cos\gamma]].$

The development of the FBP algorithm was first made [13] for the equi-spaced collinear detectors case and later extended [4] for the case of equiangular rays [11]. It uses ramp filtering with $1/L^2$ weighting. It has been shown that backprojection weight of $1/L^2$, compared to $1/L$, results in worse noise and PSF uniformity throughout the image. Originally designed for a full scan trajectory, the original algorithm was later extended to short scan trajectories [16]:

$[FBP-P]\ f(x)=BPJ_{L^2}{}^P[Q_m[w_P(s,\gamma)g(s,\gamma)\cos\gamma]],$ and later [3] for circular cone-beam geometry:

$[FDK]\ f(x)=BPJ_{L^2}[Q_m[g(s,\Theta)\cos\Theta)]],\ (\cos\Theta=\cos\gamma\cos\alpha).$ The weighting function for the short scan trajectory [FBP-P] is applied before convolution, i.e., filtering was applied to weighted data subsets. Because of this, each slice of all the projections in the reconstruction range needed to be re-weighted and re-convolved. An algorithm where weighting is done after convolution, would be more efficient. This is because the data would only be convolved one time for all data image slices, and then re-weighted. Hence, if weighting is applied after convolution, the number of convolutions required for reconstruction is greatly reduced. Thus, algorithms applying the weight function after convolution would provide a large computational advantage.

The Feldkamp algorithm was extended to helical trajectory [24] and later to arbitrary scan segments [18] as follows:

$[GFDK]\ f(x)=BPJ_{L^2}{}^{MHS,OS}\ [Q_m[W_{MHS,OS}(s,\gamma)g(s,\Theta)\cos\Theta]].$ A flowchart for this algorithm is shown in FIG. 13A.

The algorithms discussed above are limited to circular or helical source trajectories. An algorithm that is not limited to circular or helical trajectories would be advantageous. This would provide for a more versatile algorithm as it could be applied to other trajectories, e.g., saddle trajectories.

Katsevich [5, 7] introduced an exact cone-beam algorithm of the FBP type.

[Katsevich]

$$f(x) = BPJ_L^\pi\left[H_m^{Kat}\left[\left(\frac{\partial}{\partial s}+\frac{\partial}{\partial\Theta}\right)g(s,\Theta)\right]\right].$$

Instead of conventional ramp filtering it employs modified Hilbert transform of the partial derivative of the cone-beam data. A flowchart for this algorithm is shown in FIG. 13C. Katsevich later generalized his formula to one without the $\partial/\partial s$ term, and also developed an algorithm for the $3\pi$ case. In the above algorithm, filtering has to be performed in the special family of filtering lines [12], which require additional non-trivial rebinning steps before and after convolution. FIGS. 8D-8F illustrate the family of Katsevich filtering lines. For practical purposes, however, the generalized Feldkamp algorithm works quite well, and such a complication is not required for modern scanners with a relatively small number of detector rows. But Hilbert-filtering-based reconstruction provides some very nice properties lacking in the Feldkamp algorithm [3]. Katsevich's algorithm, when compared to the Feldkamp algorithm, reveals that Hilbert-filtering based reconstruction provides some very nice properties.

A fan-beam reconstruction algorithm based on Hilbert transform reconstruction was later introduced [15]:

[NDCK-FB]

$$f(x) = BPJ_L^\Lambda\left[w_N(s,\gamma)H_m\left[\left(\frac{\partial}{\partial s}+\frac{\partial}{\partial\gamma}\right)g(s,\gamma)\right]\right].$$

Reference [15] points out that for exact reconstruction, only projections that cover $\Lambda=\pi$ are required. This opens a possibility to less-than-a-short-scan reconstruction. For a short scan reconstruction the set of projections over the whole FOV is required ($\pi+2\gamma_m$). Also, the data sufficiency condition is relaxed. The other advantage of the [NDCK-FB] algorithm is that weighting of redundant fan-beam data is performed after convolution. This makes the [NDCK-FB] algorithm much more efficient compared to any Feldkamp-type algorithm since data does not have to be re-convolved for each slice.

Another advantage of Noo's algorithm was discovered during the inventors' evaluation of the noisy water cylinder phantom. It turns out that noise variance is more uniform throughout the image compared to the Feldkamp algorithm. The PSF is also less space variant for Noo's algorithm. This can be explained by the fact that the backprojection weight is the inverse distance, not the inverse distance squared, and the so-called magnification effect is reduced.

Hilbert-transform-based algorithms introduced stronger smoothing compared to algorithms using ramp filtering [8] due to an additional numerical differentiation step. Kudo [8] proposed an algorithm for fan and cone-beam data that consists of both ramp and Hilbert filtering:

[KNDC]
$$f(x) = BPJ_{L^2}^\Lambda \left[ w_N(s,\gamma) Q_m[g(s,\gamma)\cos\gamma] + \frac{\partial w_N(s,\gamma)}{\partial \gamma} H_m[g(s,\gamma)\cos\gamma] \right].$$

In reference [10] the two algorithms [NDCK-FB] and [KNDC-FB] were generalized to cone-beam case with a flat detector as follows:

[KRND-1]
$$f(x) = BPJ_L^\Lambda \left[ w_N(s,\gamma) H_m^{\mathrm{Tan}} \left[ \left( \frac{\partial}{\partial s} + \frac{\partial}{\partial \Theta} \right) g(s,\Theta) \right] \right] \text{ and}$$

[KRND-2]
$$f(x) = BPJ_{L^2}^\Lambda \left[ w_N(s,\gamma) Q_m^{\mathrm{Tan}}[g(s,\Theta)\cos\Theta] + \frac{\partial w_N(s,\gamma)}{\partial \gamma} H_m^{\mathrm{Tan}}[g(s,\Theta)\cos\Theta] \right].$$

There are several disadvantages to Kudo's algorithm. First, it is similar to Feldkamp's algorithm with its disadvantages of inverse square weight and only being workable with a particular weighting function. Second, Kudos' algorithm involves taking the partial derivative of the weight function, which makes this algorithm less appealing for practical purposes. Except for Katsevich's algorithms, the above algorithms are exact for a fan-beam scan on circular trajectory and are approximate for a cone-beam scan.

Known reconstruction algorithms suffer from several disadvantages. None of the above discussed algorithms have all of the following aspects that have been shown to be beneficial: (1) 1/L backprojection weight, (2) the redundancy compensation weight function being applied after convolution, (3) the algorithm being independent of the type of weight function used, (4) the algorithm being independent of the source trajectory, and (5) the incorporation of hybrid filtering (both ramp-type filtering and Hilbert-type filtering).

SUMMARY OF THE INVENTION

Accordingly, to overcome the problems of the reconstruction algorithms of the related art, the present invention seeks to provide a method, system, and computer program product for determining an image data value at a point of reconstruction in a computed tomography image of a scanned object.

Accordingly, there is provided a method, system, and a computer program product for determining an image data value at a point of reconstruction in a computed tomography image of a scanned object comprising: (1) obtaining projection data of the scanned object; (2) filtering the obtained projection data with a one-dimensional ramp-type filter to generate ramp-filtered data; and (3) applying a backprojection operator with inverse distance weighting to the ramp-filtered data to generate the image data value at the point of reconstruction in the CT image.

Further, according to an embodiment of the present invention, the above method further comprises: applying projection subtraction to the obtained projection data to generate subtracted data; applying a Hilbert-type filter to the subtracted data to generate Hilbert-filtered data; applying projection addition to the Hilbert-filtered data and the ramp-filtered data to generate filtered data; and applying redundancy weighting to the filtered data to generate weighted data, wherein the step of applying the backprojection operator is applied to the weighted data to generate the image data value at the point of reconstruction in the CT image.

According to another aspect of the present invention there is provided an X-ray computed tomography (CT) system for determining an image data value at a point of reconstruction, comprising: (1) a CT scanning unit configured to generate projection data of a scanned object, the scanning unit including an X-ray source configured to generate X-rays and a detector having detector elements configured to produce the projection data; and (2) a processor, including: a filtering unit configured to apply a ramp-type filter to the projection data to generate ramp-filtered data; and a backprojecting unit configured to apply a backprojection operator with inverse distance weight to the ramp filtered data to generate the image data value at the point of reconstruction.

Further, according to an embodiment of the present invention, the above system further comprises: a projection subtraction unit configured to apply a projection subtraction to the projection data to generate subtracted data; a Hilbert filtering unit configured to apply a Hilbert-type filter to the subtracted data to generate Hilbert-filtered data; a projection addition unit configured to apply projection addition to the Hilbert-filtered data with the ramp-filtered data to generate filtered data; and a weighting unit configured to apply redundancy weighting to the filtered data to generate weighted data, wherein the backprojecting unit is configured to apply a backprojection operator with inverse distance weight to the weighted data generated by the weighting unit.

Other methods, systems, and computer program products of the present invention will become apparent to one or ordinary skill in the art upon examination of the following drawings and detailed description of the preferred embodiments.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 9B is a system for carrying out the method illustrated in FIG. 9A.

FIG. 11 is a table describing the different source trajectories, projection ranges, weight functions, and filtering directions that can be used in the present invention;

FIGS. 13A-13D illustrate four reconstruction algorithms.

DETAILED DESCRIPTION OF THE PREFERRED EMBODIMENTS

The present invention is directed to exact algorithms for fan-beam data and quasi-exact algorithms for cone-beam data. These algorithms are used in the reconstruction of images taken with a CT device. Embodiments of the present invention are given below.

$2\pi$ Projection Range (Full-Scan) Formula for Fan-Beam Data:

$$f(x) = \frac{1}{4\pi} \int_{-\pi}^{\pi} \frac{1}{L(s,x)} Q_{mo}[g(s,\gamma)]_{\gamma=\gamma(s,x)} ds$$

$$f(x) = BPJ_L^{2\pi}[Q_{mo}[g(s,\gamma)]].$$

Flexible Projection Range, Super-Short-Scan, Short-Scan or Over-Scan Formula for Fan-Beam Data:

$$f(x) = \frac{1}{2\pi} \int_{\Lambda} \frac{w(s,\gamma)}{L(s,x)} \left[ Q_{mo}[g(s,\gamma)] + H_m\left[\frac{\partial}{\partial s}g(s,\gamma)\right] \right]_{\gamma=\gamma(s,x)} ds$$

$$f(x) = BPJ_L^{\Lambda}\left[ w(s,\gamma)\left( Q_{mo}[g(s,\gamma)] + H_m\left[\frac{\partial}{\partial s}g(s,\gamma)\right]\right)\right]$$

$2\pi$ Projection Range (Full-Scan) Formula for Cone-Beam Data:

$$f(x) = \frac{1}{4\pi} \int_{-\pi}^{\pi} \frac{1}{L(s,x)} Q_{mo}[g(s,\gamma,\alpha)]_{\gamma=\gamma(s,x),\alpha=\alpha(s,x)} ds$$

$$f(x) = BPJ_L^{2\pi}[Q_{mo}[g(s,\Theta)]]$$

Flexible Projection Range, Super-Short-Scan, Short-Scan or Over-Scan Formula for Cone-Beam Data:

$$f(x) = \\ \frac{1}{2\pi} \int_{\Lambda} \frac{w(s,\gamma)}{L(s,x)} \left[ Q_{mo}[g(s,\gamma,\alpha)] + H_m\left[\frac{\partial}{\partial s}g(s,\gamma,\alpha)\right] \right]_{\gamma=\gamma(s,x),\alpha=\alpha(s,x)} ds$$

$$f(x) = BPJ_L^{\Lambda}\left[ w(s,\gamma)\left( Q_{mo}[g(s,\Theta)] + H_m\left[\frac{\partial}{\partial s}g(s,\Theta)\right]\right)\right]$$

Cone Beam Data Reconstruction from Tam Window:

$$f(x) = BPJ_L^{TW}\left[\left( Q_{mo}[g(s,\Theta)] + H_m\left[\frac{\partial}{\partial s}g(s,\Theta)\right]\right)\right]$$

$$f(x) = BPJ_L^{ETW}\left[\left( Q_{mo}[g(s,\Theta)] + H_m\left[\frac{\partial}{\partial s}g(s,\Theta)\right]\right)\right]$$

The above embodiments of the present invention are given for an equi-angular detector. The algorithms of the present invention are not restricted only to an equi-angular detector, but work with other detector geometries, such as a collinear detector, an equi-spaced detector, a non-equi-spaced detector, a flat detector, a cylindrical detector, a spherical detector, a tilted, and a PI-masked detector.

Further, the algorithms of the present invention work independent of the source trajectory. Source trajectories need not be limited to circular or helical trajectories. For example, saddle trajectories can be applied.

Figure 1:
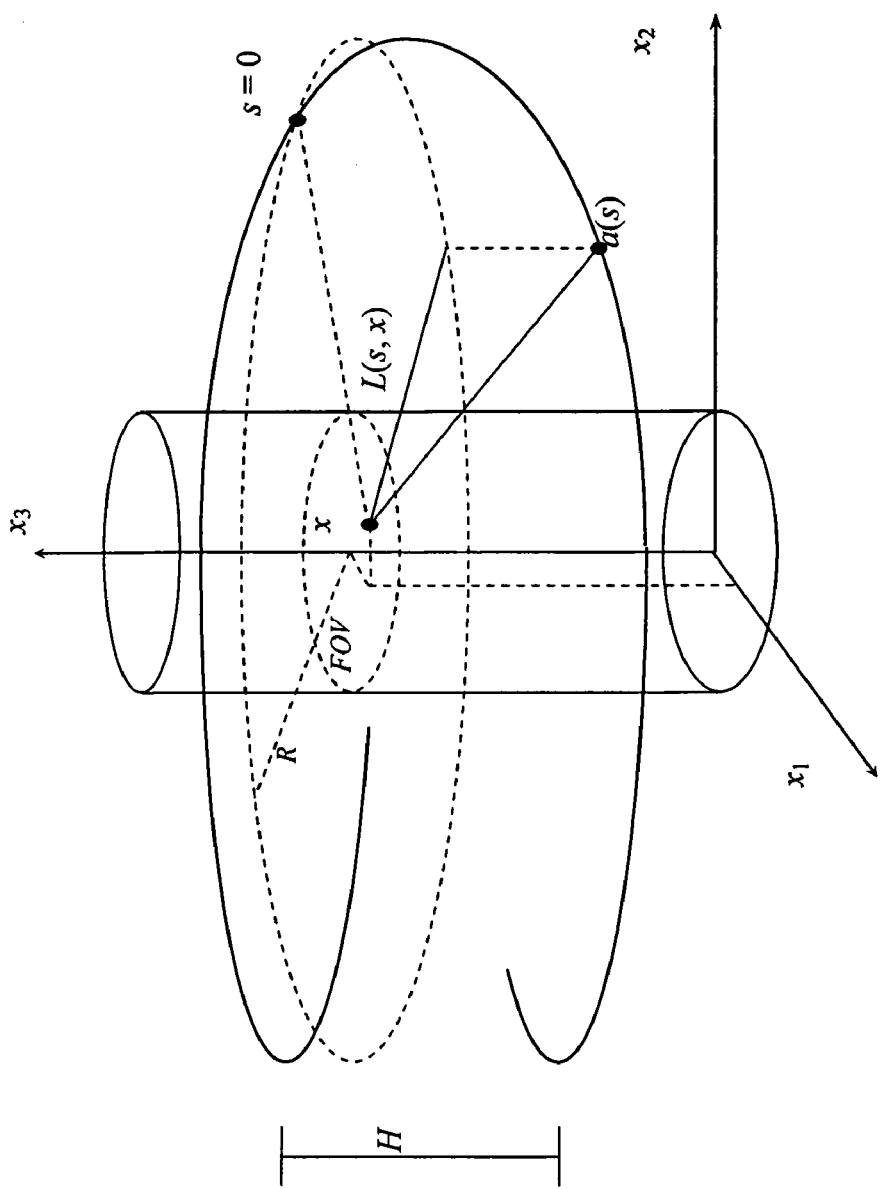
FIG. 1 illustrates a source trajectory with helical geometry.
Figure 2:
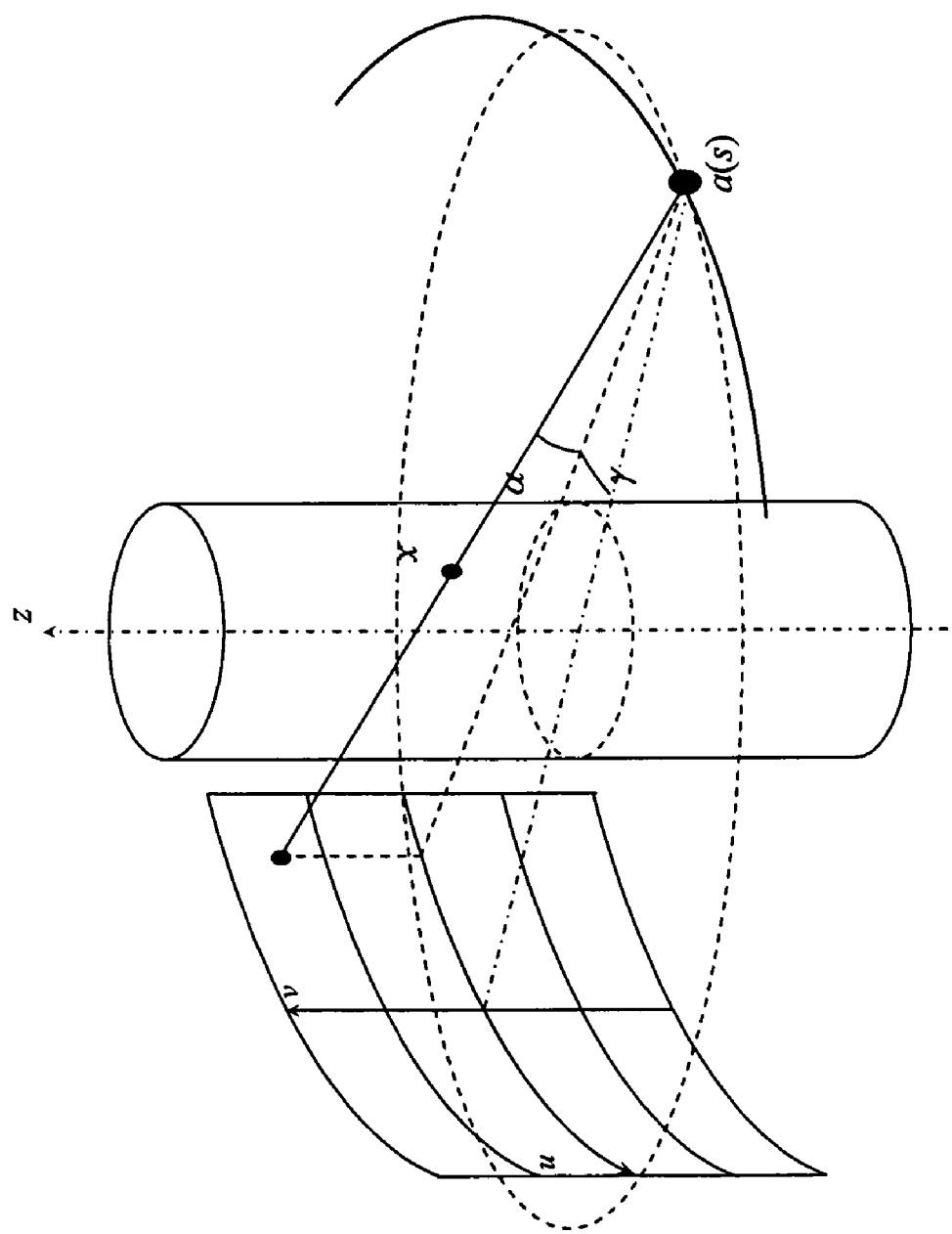
FIG. 2 illustrates an equi-angular cylindrical detector.
Figure 3:
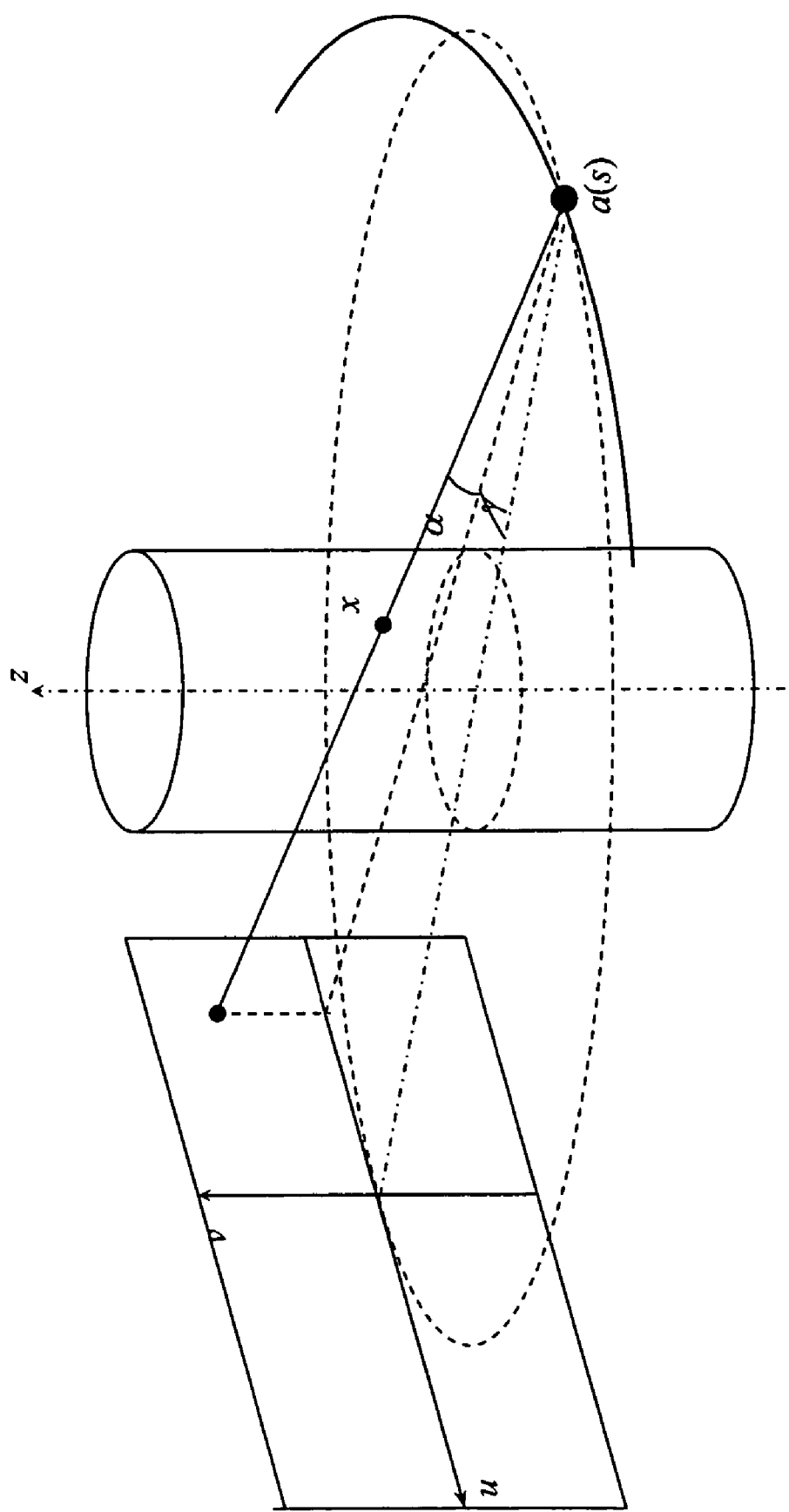
FIG. 3 illustrates a collinear detector.
Figure 4A:
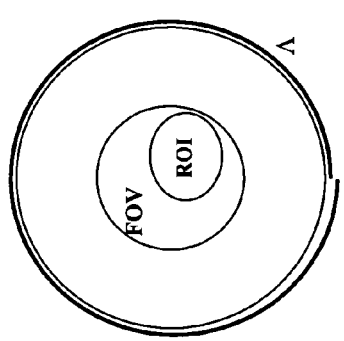
FIGS. 4A-4E illustrate a full scan, over-scan, short scan, super-short scan and flexible reconstruction ranges, respectively.
Figure 4B:
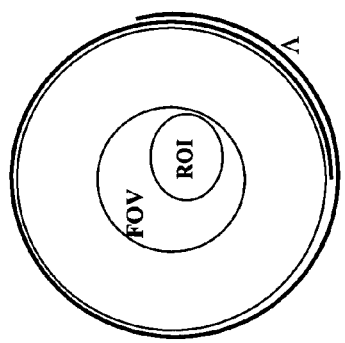
Figure 4C:
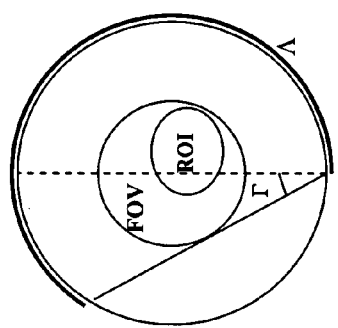
Figure 4D:
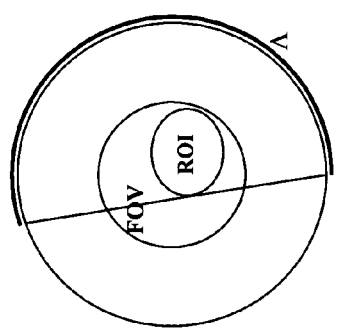
Figure 4E:
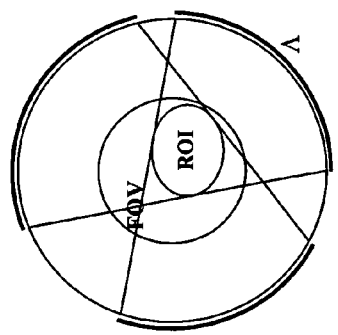
Figure 5:
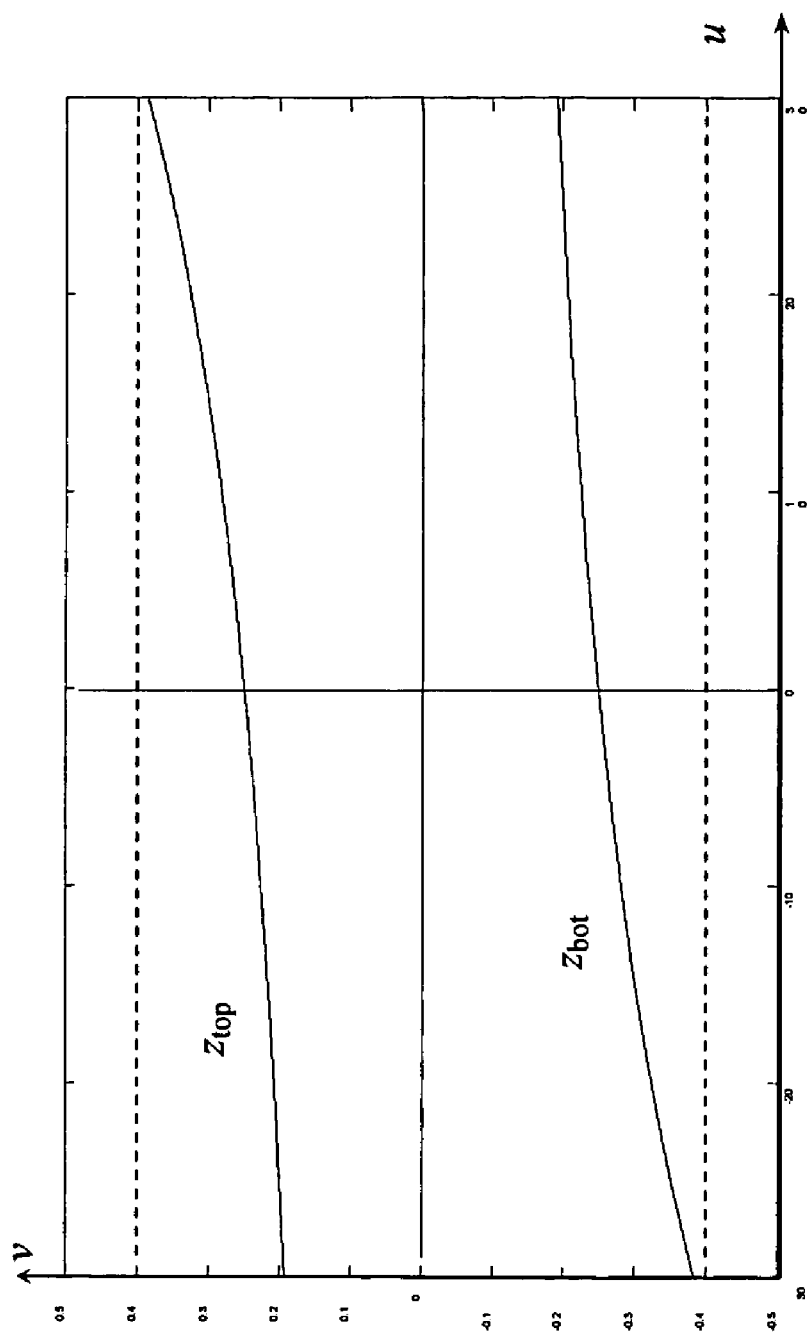
FIG. 5 illustrates a π Tam window.
Figure 6:
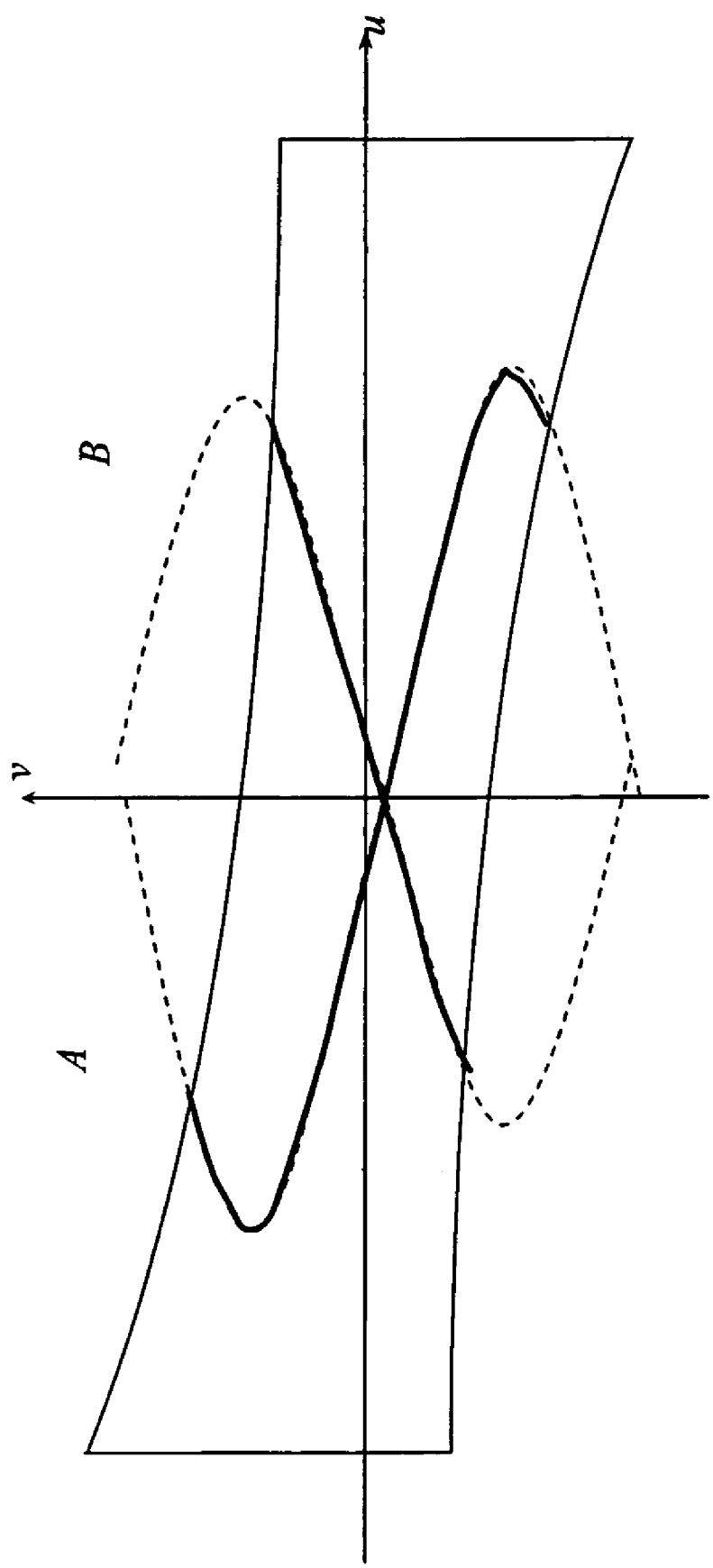
FIG. 6 illustrates a Tam window reconstruction range.
Figure 7:
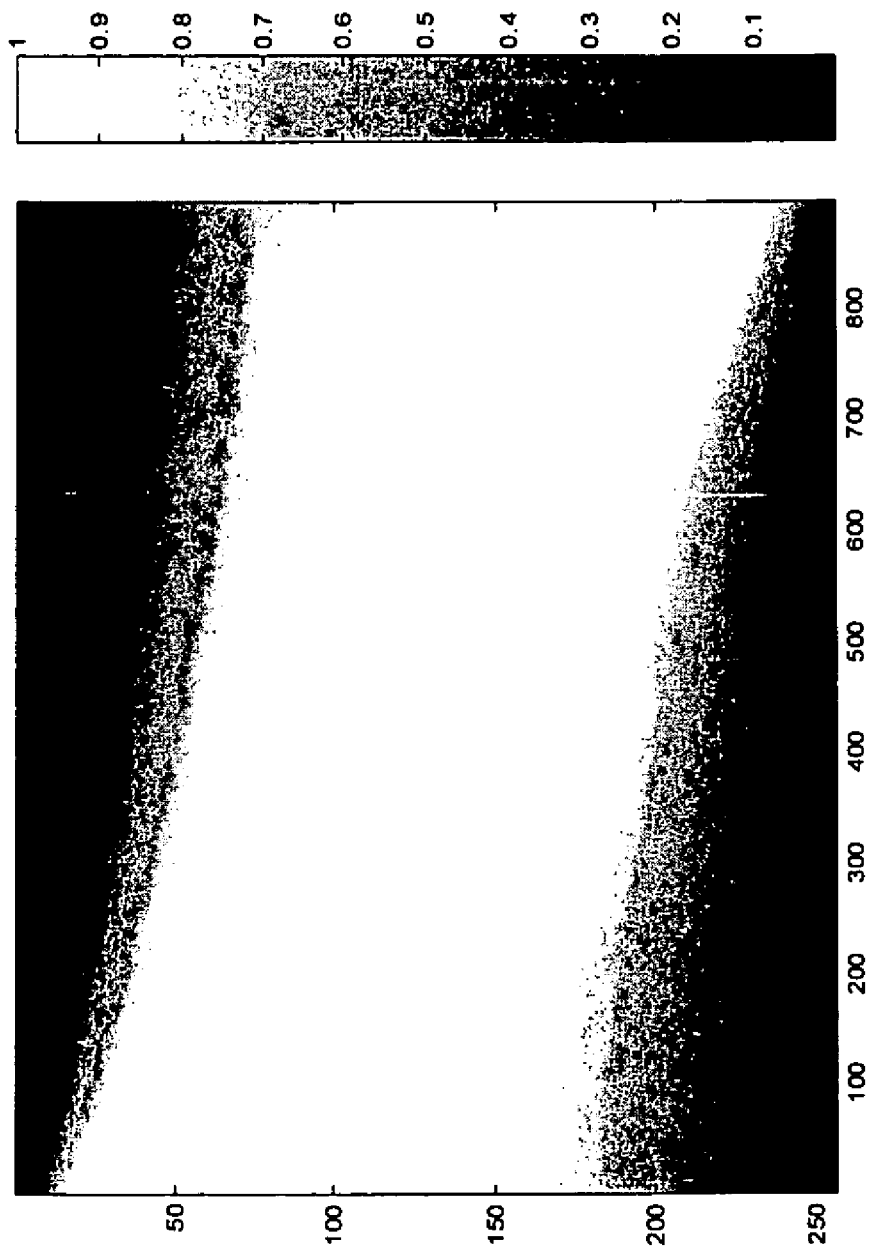
FIG. 7 illustrates an extended Tam Window.
Figure 8C:
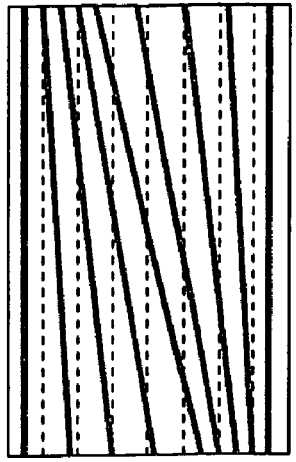
FIGS. 8A-8F illustrate filtering lines.
Figure 8B:
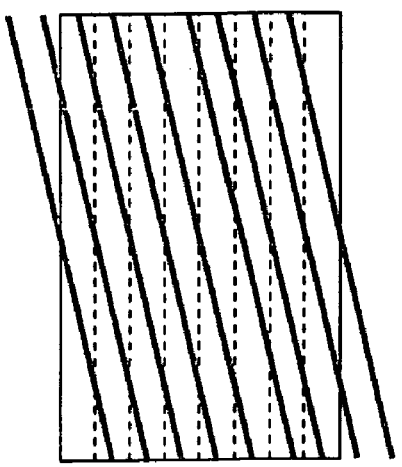
Figure 8A:
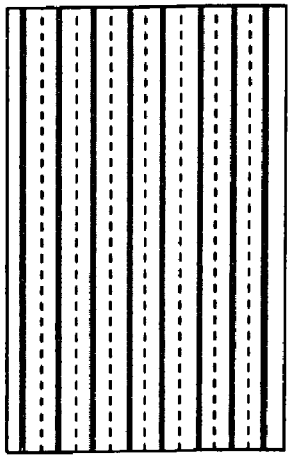
Figure 8F:
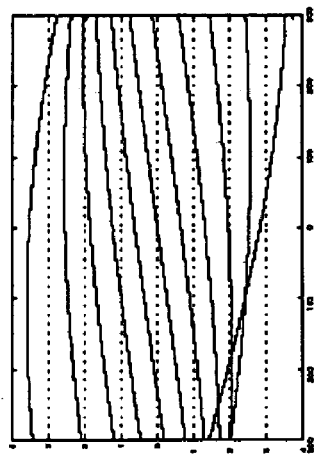
Figure 8E:
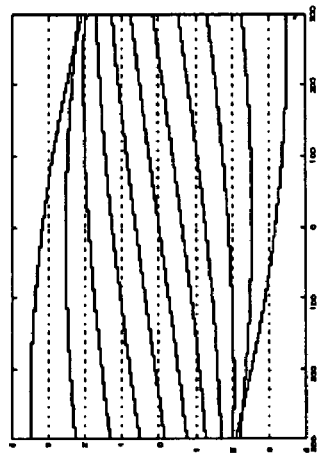
Figure 8D:
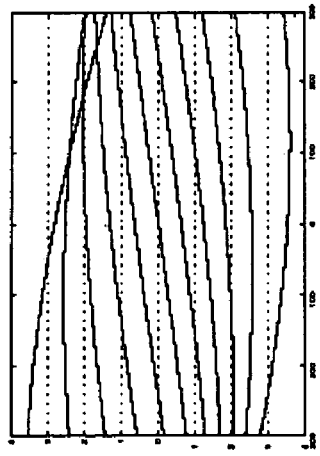
Figure 9A:
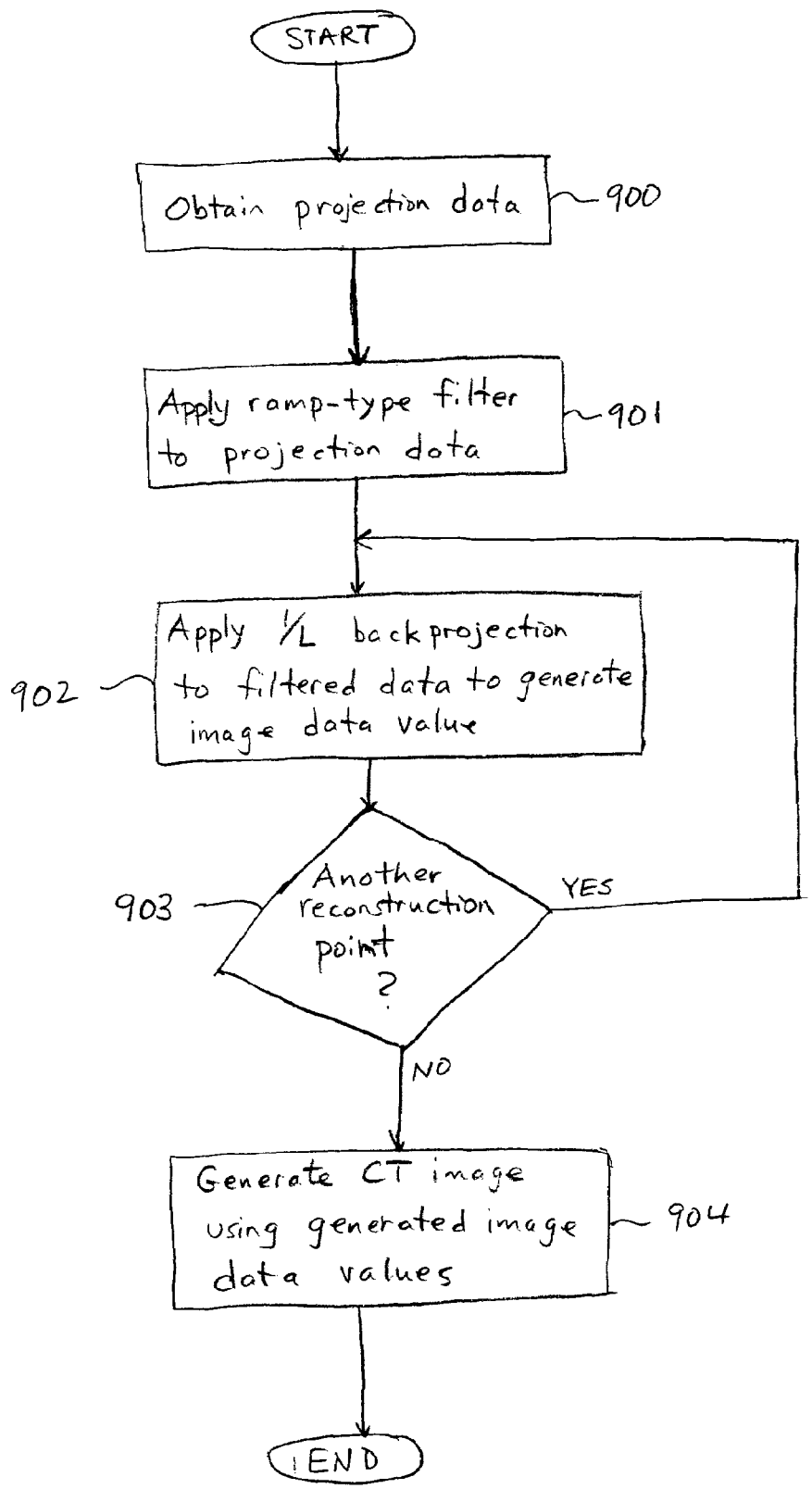
FIG. 9A illustrates a method determining an image data value at a point of reconstruction for a fill scan according to the present invention.

FIG. 9A illustrates an embodiment of the reconstruction algorithm of the present invention for a full scan. In step 900, CT projection data is obtained by known methods. The function $g(s,\gamma)$ or $g(s,\Theta)$) is the projection data illustrated in step 900 of FIG. 9A for fan-beam data or cone-beam data, respectively.

In step 901, the data is filtered with a ramp-type filter to generate filtered data. This ramp-type filter may be a ramp filter, a modified ramp filter, or a modified ramp filter with a DC offset.

In step 902, a 1/L weighted backprojection is applied to the ramp filtered data to produce an image data value in the CT image.

In step 903, a determination is made whether there are other image data values to be reconstructed in the CT image. If there are other image data values, step 902 is repeated until there are no other image data values to be reconstructed in the CT image.

In step 904, the image values outputted from step 902 are used to generate the CT image by arranging the image data values according to the points of reconstruction.

FIG. 9B illustrates a system for reconstructing image data values in a CT image. CT scanning unit 951 generates projection data. The CT scanning unit can either transfer the projection data to processor 960 or to storage unit 952. Processor 960 is configured to receive the projection data either directly from the CT scanning unit 951 or access it from storage unit 952. Processor 960 includes a filtering unit 961, a backprojection unit 962 and an output unit 963. Filtering unit 961 is configured to apply a ramp-type filter to the projection data to generate ramp-filtered data. Backprojection unit 962 is configured to apply a backprojection operator, with 1/L weighting, to the ramp-filtered data to generate an image data value at a point of reconstruction. Output unit 963 then outputs the image data value to display 970, storage unit 971, or both. Ramp filtering unit 961 and backprojecting unit 962 are both capable of storing and retrieving information from storage unit 952.

Figure 10A:
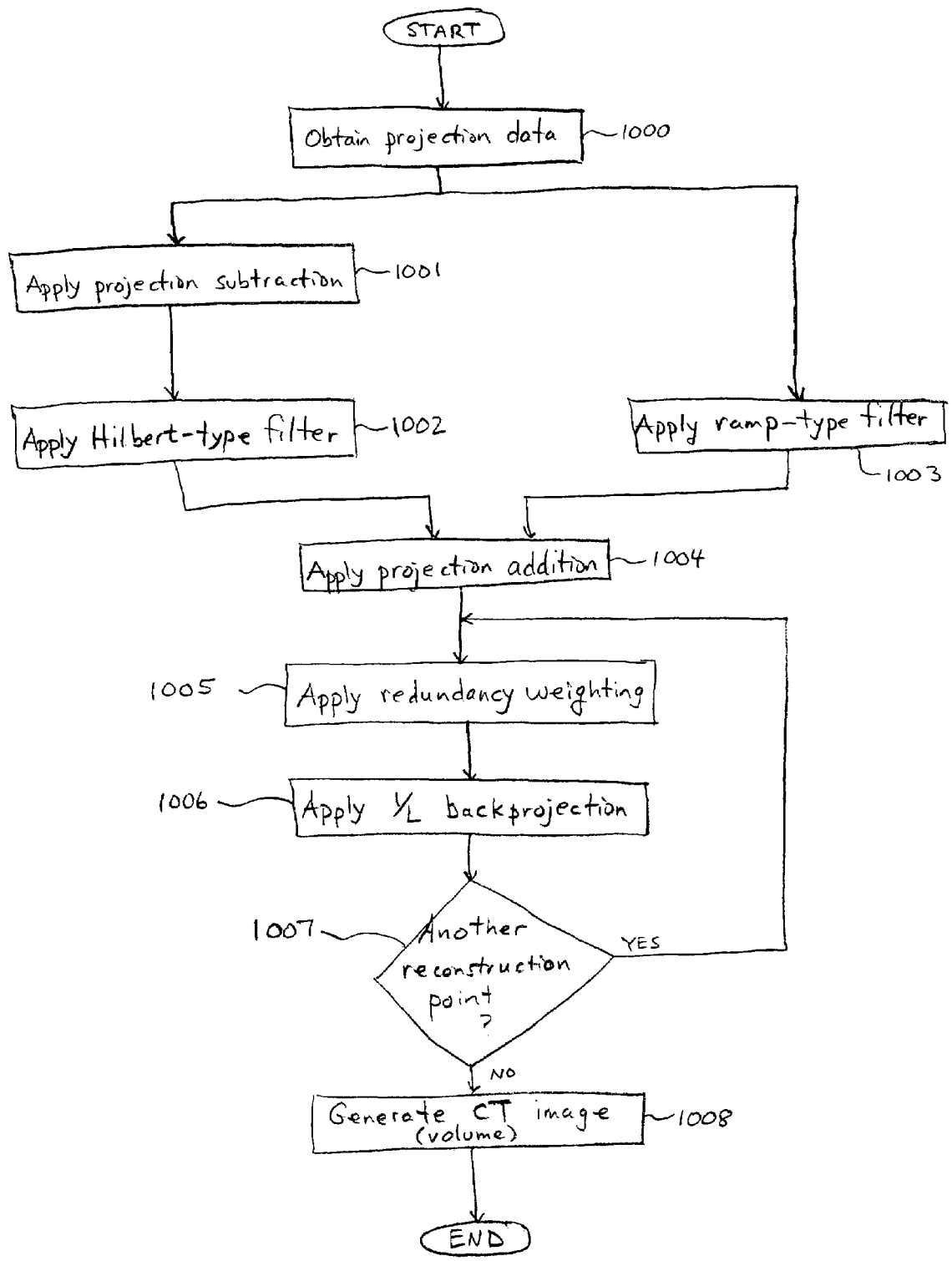
FIG. 10A illustrates a method of determining an image data value at a point of reconstruction for a flexible projection range, super-short projection range, a short-scan, or an over scan according to the present invention.

FIG. 10A illustrates another embodiment of the reconstruction algorithm of the present invention. The fan-beam and cone-beam formulas for flexible range, super short-scan, short-scan or over-scan use $g(s,\gamma)$ or $g(s,\Theta)$) to represent the projection data shown in step 1000 of FIG. 10A for fan-beam or cone-beam data respectively.

In step 1001, projection subtraction is applied to the projection data to generate subtracted data. Projection subtraction is the application of the partial derivative term in the above algorithm of the present invention.

In step 1002, a Hilbert filter is applied to the subtracted data to generate Hilbert-filtered data. In step 1002, either a Hilbert filter or a modified Hilbert filter may be applied.

In step 1003, a ramp filter is applied to the projection data to generate ramp-filtered data.

In step 1004, the Hilbert-filtered data and the ramp-filtered data are combined to generate filtered data.

In step 1005, a redundancy weighting function is applied to the filtered data. The redundancy weighting function w(s, γ) is not specified in the proposed reconstruction algorithms, and can be chosen freely from Parker weighting, generalized Parker weighting (MHS), Noo's weighting, over-scan weighting, quasi cone-beam weighting, and Tam window weighting $\{w_P(s,\gamma), W_{MHS}(s, \gamma), w_N(s, \gamma), w_{OS}(s, \gamma), W_{3D}(s, \gamma), w_T(\gamma, v)\}$.

FIG. 11 is a table that includes which weighting functions are used with which type of beam data. FIG. 11 shows how the algorithms of the present invention, for both fan-beam data and cone-beam data, work with different source trajectories, different detector geometries, what projection ranges can be used, what weighting functions can be used, and what filtering direction can be used. The projection range, Λ, will determine the choice of weighting function. For fan-beam data, a super-short scan will use Noo weighting; a short scan will use either Parker weighting, MHS weighting, or Noo weighting; an over-scan will use either OS weighting or Noo weighting; and a flexible scan will use Noo weighting. Cone-beam data is the same as fan-beam data, except that when the projection range is either a short-scan or an over-scan Q3D weighting can be used. Tam window weighting can also be used with cone-beam data.

In step 1006, the weighted data is subjected to a back-projection operator with an inverse distance weighting to generate an image data value.

In step 1007, a determination is made whether there are other image data values to be reconstituted in the CT image. If there are other image data values, steps 1005-1007 are repeated until there are no other image data values in the CT image.

In step 1008, the image data values are outputted to generate a CT image by arranging the image data values according to the points of reconstruction.

Figure 10B:
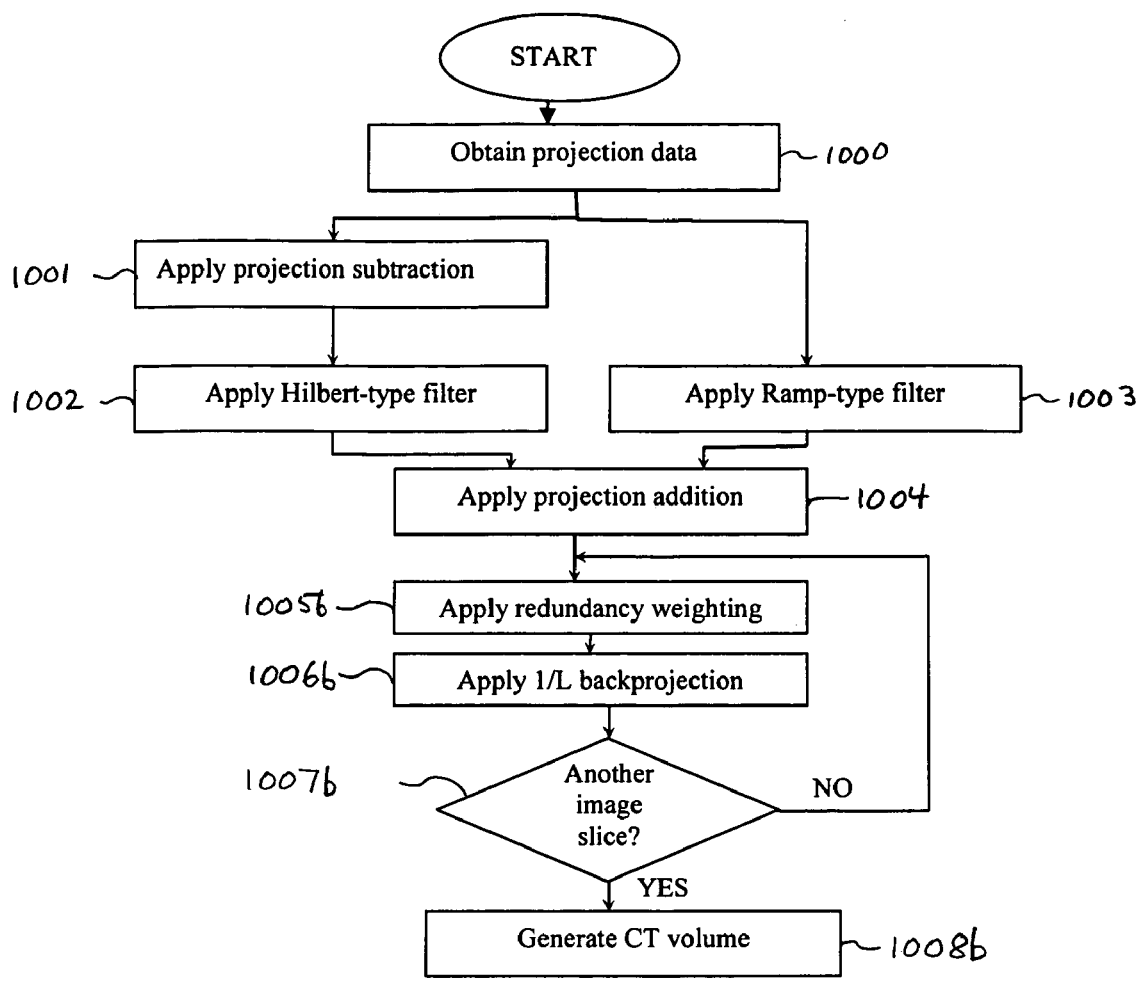
FIG. 10B illustrates a method of determining image data values for an image slice according to the present invention.

FIG. 10B illustrates another embodiment of the reconstruction algorithm of the present invention in which image data values are reconstructed on a slice-by-slice basis. The fan-beam and cone-beam formulas for flexible range, super short-scan, short-scan or over-scan use g(s, γ) or g(s, Θ) to represent the projection data shown in step 1000 of FIG. 10B for fan-beam or cone-beam data, respectively.

In step 1001, projection subtraction is applied to the projection data to generate subtracted data. Projection subtraction is the application of the partial derivative term in the above algorithm of the present invention.

In step 1002, a Hilbert filter is applied to the subtracted data to generate Hilbert-filtered data. In step 1002, either a Hilbert filter or a modified Hilbert filter may be applied.

In step 1003, a ramp filter is applied to the projection data to generate ramp-filtered data.

In step 1004, the Hilbert-filtered data and the ramp-filtered data are combined to generate filtered data.

In step 1005b, a redundancy weighting function is applied to the filtered data for a particular slice represented by a common axial (z) coordinate. The redundancy weighting function w(s, γ) is not specified in the proposed reconstruction algorithms, and can be chosen freely from Parker weighting, generalized Parker weighting (MHS), Noo's weighting, over-scan weighting, quasi cone-beam weighting, and Tam window weighting $\{w_P(s,\gamma), W_{MHS}(s, \gamma), w_N(s, \gamma), w_{OS}(s, \gamma), w_{3D}(s, \gamma), w_T(\gamma, v)\}$.

In step 1006b, the weighted data is subjected to a back-projection operator with an inverse distance weighting based on the given z-coordinate of the slice to generate an image data value.

In step 1007b, a determination is made whether there are other z coordinates corresponding to other image slices to be reconstituted in the CT image volume. If there are other slices to be reconstructed, steps 1005b-1007b are repeated until there are no image slices to be reconstructed in the CT image volume.

In step 1008b, the image data values in each slice are outputted to generate a CT image volume by arranging the image data values according to the points of reconstruction in each slice.

Figure 10C:
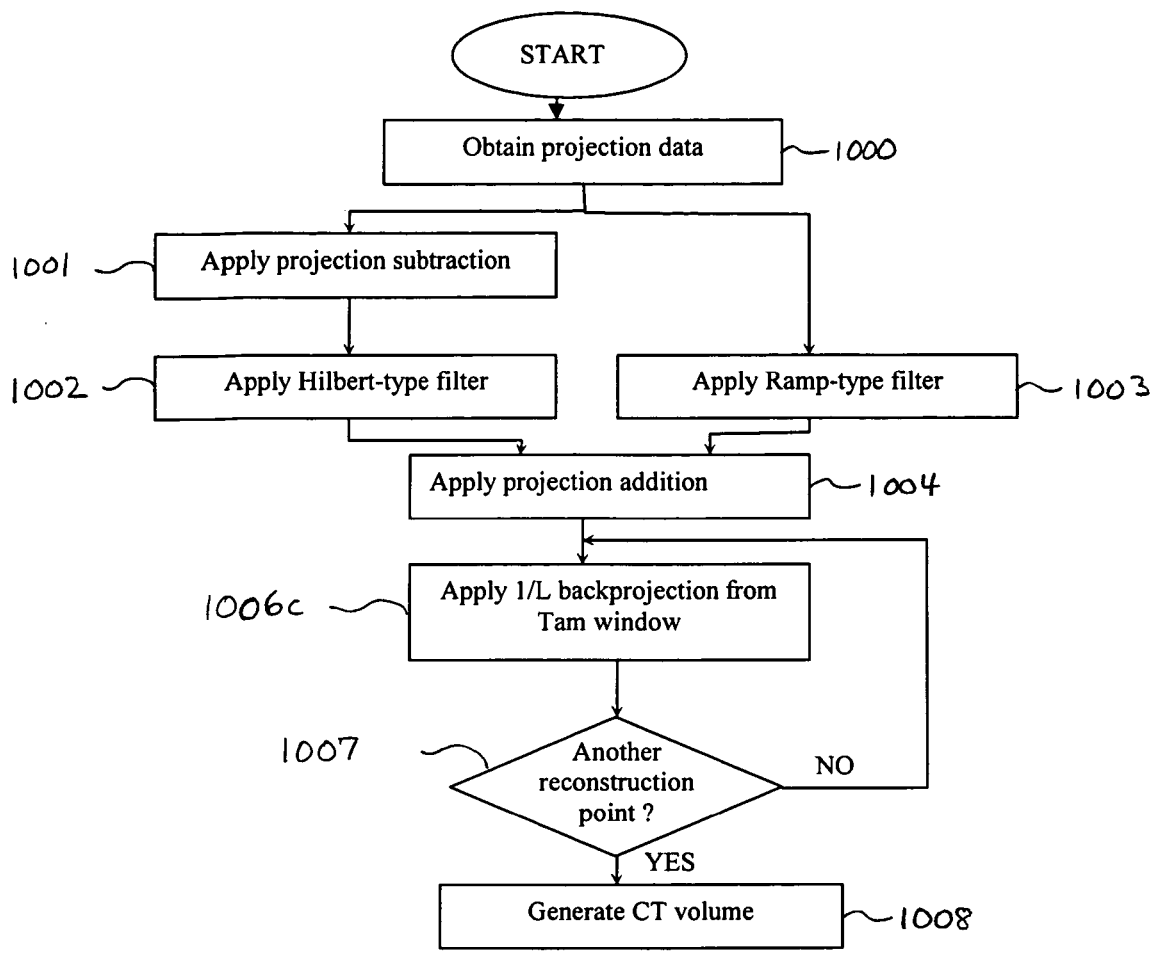
FIG. 10C illustrates a method of determining an image data value at a point of reconstruction using 1/L backprojection from a Tam window.

FIG. 10C illustrates another embodiment of the reconstruction algorithm of the present invention. The fan-beam and cone-beam formulas for flexible range, super short-scan, short-scan or over-scan use g(s, γ) or g(s, Θ)) to represent the projection data shown in step 1000 of FIG. 10C for fan-beam or cone-beam data respectively.

In step 1001, projection subtraction is applied to the projection data to generate subtracted data. Projection subtraction is the application of the partial derivative term in the above algorithm of the present invention.

In step 1002, a Hilbert filter is applied to the subtracted data to generate Hilbert-filtered data. In step 1002, either a Hilbert filter or a modified Hilbert filter may be applied.

In step 1003, a ramp filter is applied to the projection data to generate ramp-filtered data.

In step 1004, the Hilbert-filtered data and the ramp-filtered data are combined to generate filtered data.

In step 1006c, the filtered data is subjected to a backprojection operator with an inverse distance weighting using a Tam window to generate an image data value. In particular, backprojection is restricted to filtered data contained within the Tam window only, as discussed above.

In step 1007, a determination is made whether there are other image data values to be reconstituted in the CT image. If there are other image data values, steps 1005-1007 are repeated until there are no other image data values in the CT image.

In step 1008, the image data values are outputted to generate a CT image by arranging the image data values according to the points of reconstruction.

Figure 10D:
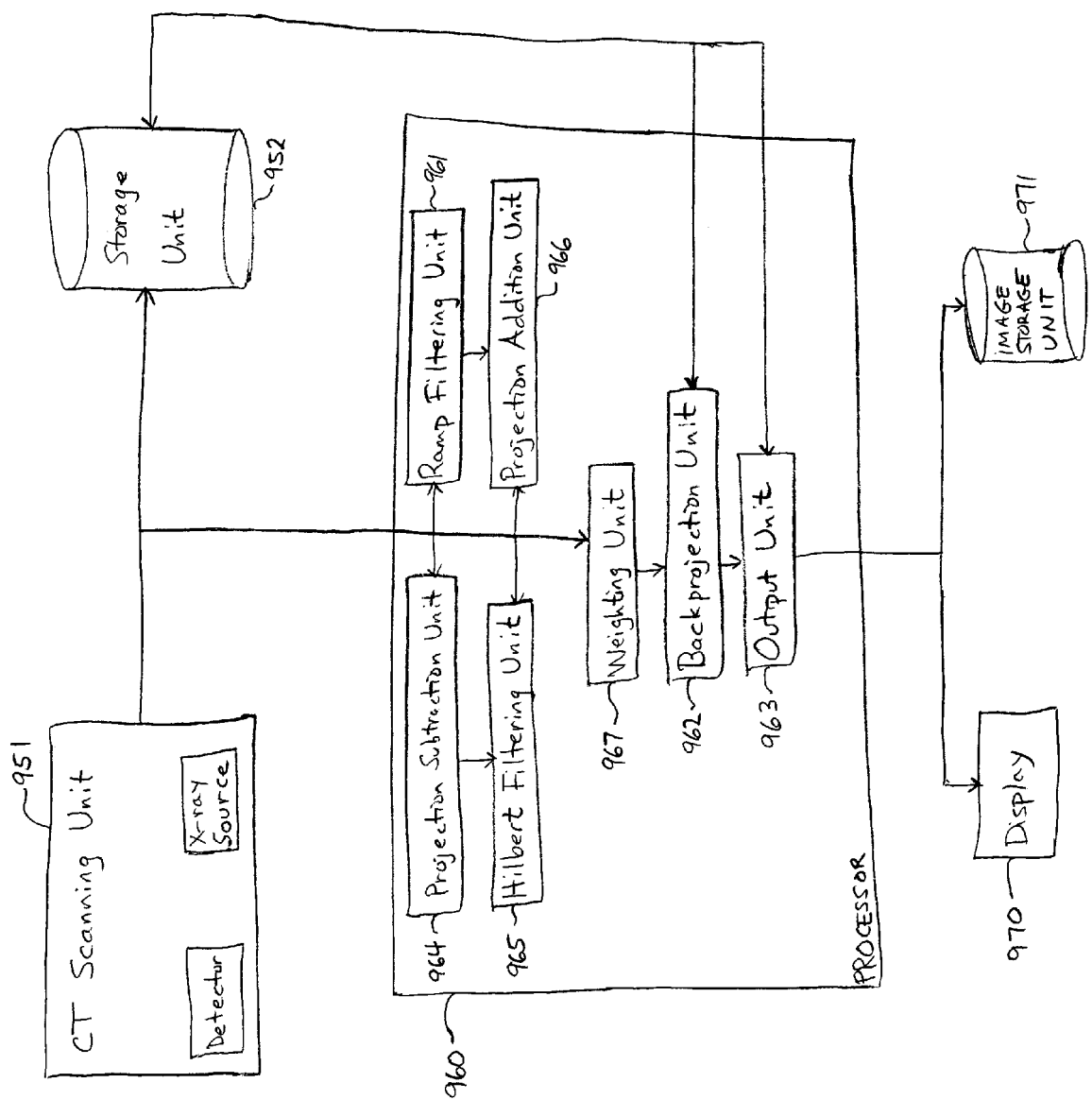
FIG. 10D is a system for carrying out the methods of FIGS. 10A, 10B, and 10C.

FIG. 10D illustrates a system for processing data image values in a CT image. CT scanning unit 951 obtains either fan-beam or cone-beam data. The CT scanning unit can either transfer the beam data to processor 960 or to storage unit 952. Processor 960 will receive the beam data either directly from the CT scanning unit 951 or access it from storage unit 952. Processor 960, in this embodiment, includes ramp filtering device 961, projection subtraction unit 964, Hilbert filtering unit 965, projection addition unit 966, weighting unit 967, backprojection unit 962, and outputting unit 963. Projection subtraction unit 964 applies projection subtraction to the beam data that comes from either the CT scanning unit 951 or storage unit 952 to generate subtracted data. Hilbert filtering unit 965 then applies a Hilbert-type filter to the subtracted data to generate Hilbert-filtered data. Ramp filtering unit 961 applies a ramp-type filter to the beam data obtained from either CT scanning unit 951 or storage unit 952 to generate ramp filtered data. Projection addition unit 966 combines the ramp filtered data with the Hilbert-filtered data to generate filtered data. Weighting unit 967 applies a weighting function to the filtered data to generate weighted data. Backprojection unit 962 applies a backprojection operator with 1/L weighting to the weighted data to generate a data image value according to the points of reconstruction. Outputting unit 963 outputs this data image value to display 970, storage 971 or both. The Hilbert filtering unit 965, projection addition unit 966, weighting unit 967, backprojection unit 962, and outputting unit 963 are all capable of storing and retrieving information from storage unit 952.

The embodiments described here can be applied with circular, helical, or saddle trajectories. The algorithms are independent of the geometry of the detector, i.e. equi-angular, equi-spaced, non-equi-spaced, flat, cylindrical, spherical, tilted, rotated, PI-masked, etc. can be used. The formulas are independent from the type of filtering lines used; horizontal, tangential, rotated, Katsevich or any other reasonable family of filtering lines. Super-short scan, short scan, over-scan, and any trajectory satisfying the completeness condition can be used.

Comparison of Present Invention to Other CT Image Reconstruction Algorithms

A reconstruction algorithm can be applied to a different source trajectory, a different detector geometry, use a different filtering direction, and use a different weighting function. However, reconstruction flow and major steps are unique for each algorithm. To better see the main features of the algorithms, operator notation will be used. Equations for helical cone-beam geometry with redundancy weighting, which represent the most practical interest, will be compared. All formulas will be rewritten for equi-angular detector geometry. Flowcharts illustrating the algorithms below are shown in FIGS. 13A-D and an algorithm according to the present invention is shown in FIG. 10A.

[GFDK]

$$f(x) = BPJ_{L^2}^{MHS,OS}[Q^m[w_{MHS,OS}(s, \gamma)g(s, \Theta)\cos\Theta]]$$

[NDCK]

$$f(x) = BPJ_L^\Lambda \left[w_N(s, \gamma)H_m\left[\left(\frac{\partial}{\partial s} + \frac{\partial}{\partial \Theta}\right)g(s, \Theta)\right]\right]$$

[KRND]

$$f(x) = BPJ_{L^2}^\Lambda\left[w_N(s, \gamma)Q_m[g(s, \Theta)\cos\Theta] + \frac{\partial w_N(s, \gamma)}{\partial \gamma}H_m[g(s, \Theta)\cos\Theta]\right]$$

[Katsevich]

$$f(x) = BPJ_L^\pi\left[H_m^{Kat}\left[\left(\frac{\partial}{\partial s} + \frac{\partial}{\partial \Theta}\right)g(s, \Theta)\right]\right]$$

[an embodiment of present invention]

$$f(x) = BPJ_L^\Lambda\left[w(s, \gamma)\left(Q_0^m[g(s, \Theta)] + H^m\left[\frac{\partial}{\partial s}g(s, \Theta)\right]\right)\right]$$

Spatial uniformity depends on the backprojection weight. Algorithms with 1/L backprojection weight posses better spatial uniformity. Hence NDCK, Katsevich and the algorithm of the present invention produce more spatially uniform images than GFDK and KRND. In Katsevich's algorithm, on the other hand, different image pixels have a different projection range, which results in less spatial uniformity. FIG. 10 and FIGS. 13A-D show a block that indicates the weighting of the backprojection for each algorithm.

The discussion in this section is irrelevant for [Katsevich] since it does not have the cone-beam artifacts. All other algorithms are exact only for a fan-beam geometry with circle trajectory (i.e. in 2D). They can also provide reasonably good results for relatively small cone angles and helical pitches, by extending to 3D. However, the algorithms do not perform equally well in 3D. Cone-beam artifacts appear as shading on one side of the object and glaring on the other. [NDCK] and [KRND] are proposed with tangential filtering, which is known to reduce, but not eliminate, the cone-beam artifacts. Since tangential filtering (as well as rotated filtering) can be also applied to [GFDK] and the algorithm of the present invention, it will not be consider an advantage of only [NDCK] and [KRND]. [NDCK] and the algorithms of the present invention show less cone-beam artifact because they contain $\partial/\partial s$ term, which is the difference between neighboring projections. This compensates for the helical data inconsistency. Note that cone-beam artifact is not present in Katsevich's algorithm, which also has $\partial/\partial s$ term.

One of the main reasons for cone-beam artifact is using fan-beam redundancy weighting for helical cone-beam data. Using a Tam window redundancy weighting function helps significantly reduce cone-beam artifact. Table 1 shows which weights can be used with different algorithms.

TABLE 1

| | Redundancy weighting for different algorithms | | | |
|---|---|---|---|---|
| | OS | MHS | Noo | Tam W |
| GFDK | * | * | — | — |
| NDCK | * | * | * | * |
| KRND | * | * | * | — |
| Katsevich | — | — | — | * |
| Present Invention | * | * | * | * |

Note that only [NDCK] and the present invention work with all weights.

When comparing CT reconstruction algorithms to each other, factors such as the speed of volume reconstruction, whether there is a flexible reconstruction range and the simplicity of software implementation are important.

The speed of volume reconstruction is primarily defined by how many operations are performed in the slice reconstruction loop. In FIGS. 13A-D, the slice reconstruction loop for [GFDK] contains filtering, which means that the same projection is re-convolved many times for each image slice. All other algorithms are more efficient: each projection is convolved only once (for [NKDC] and [Katsevich]) or twice (for [KRND] and an embodiment of the present invention in FIG. 10A); no re-convolutions are required. However, the [KRND] slice reconstruction loop is more complicated than [NKDC], [Katsevich], and the present invention. Note that backprojection is the most computationally demanding part of backprojection, and only one backprojection per slice cycle is strongly desired for a commercial CT reconstructor.

Flexible reconstruction range means that any subset of the source trajectory, whose projection onto xy-plane satisfies 2D data sufficiency condition, can be used for accurate reconstruction. [NKDC], [KRND] and the present invention by construction have flexible reconstruction range. [Katsevich] does not have flexible reconstruction range since it uses Tam window weighting. Flexible reconstruction range also means a possibility of super-short scan. The algorithms that have this possibility are: [NKDC], [KRND] and the present invention.

Simplicity of implementation is crucial for a commercial CT reconstruction algorithm. One important criterion is that each step (filtering, weighting, backprojection) can be represented as a separate module. Also, angular differentiating in [NKDC] depends on how it is implemented and can become quite complicated. In the present invention, the only differentiation, $\partial/\partial s$, is a simple projection subtraction.

Numerical data differentiation results in resolution loss. In [GFDK], [KRND] and the present invention there is no loss in resolution, since the major part of the image is reconstructed from ramp-filtered data, which undergoes no derivative steps.

Table 2 shows the main features of the algorithms under consideration:

TABLE 2

| | Performance comparison | | | | | | | |
|---|---|---|---|---|---|---|---|---|
| | IQ | | | Efficiency | | | | |
| | Spatial uniformity | Resolution | Cone-beam artifacts | Weight after filtering | Flexible recon-n range | Fast volume recon | Simplicity | Score |
| FDK | — | * | — | — | — | — | * | 2/7 |
| Noo | * | — | ○ | * | * | * | ○ | 5/7 |
| Kudo | — | * | — | * | * | ○ | — | 3.5/7 |
| Katsevich | ○ | — | * | * | — | * | — | 3.5/7 |
| Proposed | * | * | ○ | * | * | * | ○ | 6/7 |

Legend:
* Yes, or 1;
○ Neutral, or .5;
— No, or 0.

Figure 12:
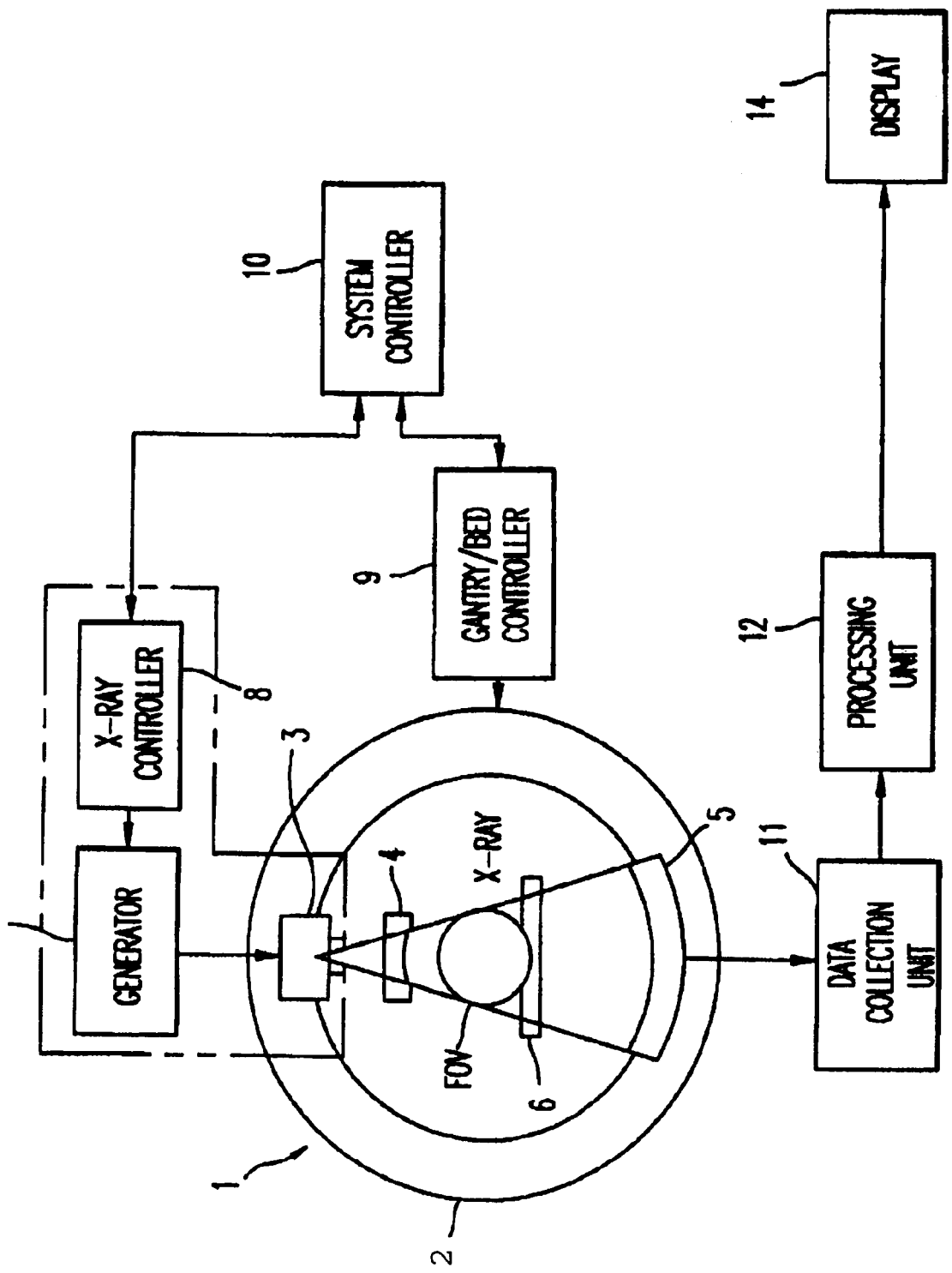
FIG. 12 illustrates a CT apparatus.

FIG. 12 shows an x-ray computed topographic imaging device that can be used to obtain data processed by methods of the present invention. The projection data measurement system constituted by gantry 1 accommodates an x-ray source 3 that generates a cone-beam of x-ray flux approximately cone-shaped, and a two-dimensional array type x-ray detector 5 consisting of a plurality of detector elements arranged in two-dimensional fashion, i.e., a plurality of elements arranged in one dimension stacked in a plurality of rows. X-ray source 3 and two-dimensional array type x-ray detector 5 are installed on a rotating ring 2 in facing opposite sides of a subject, who is laid on a sliding sheet of a bed 6. Two-dimensional array type x-ray detector 5 is mounted on rotating ring 2. Each detector element will correspond with one channel. X-rays from x-ray source 3 are directed on to subject through an x-ray filter 4. X-rays that have passed through the subject are detected as an electrical signal by two-dimensional array type x-ray detector 5.

X-ray controller 8 supplies a trigger signal to high voltage generator 7. High voltage generator 7 applies high voltage to x-ray source 3 with the timing with which the trigger signal is received. This causes x-rays to be emitted from x-ray source 3. Gantry/bed controller 9 synchronously controls the revolution of rotating ring 2 of gantry 1 and the sliding of the sliding sheet of bed 6. System controller 10 constitutes the control center of the entire system and controls x-ray controller 8 and gantry/bed controller 9 such that, as seen from the subject, x-ray source 3 executes so-called helical scanning, in which it moves along a helical path. Specifically, rotating ring 2 is continuously rotated with fixed angular speed while the sliding plate is displaced with fixed speed, and x-rays are emitted continuously or intermittently at fixed angular intervals from x-ray source 3.

The output signal of two-dimensional array type x-ray detector 5 is amplified by a data collection unit 11 for each channel and converted to a digital signal, to produce projection data. The projection data that is output from data collection unit 11 is fed to reconstruction processing unit 12. Reconstruction processing unit 12 uses the projection data to find backprojection data reflecting the x-ray absorption in each voxel. In the helical scanning system using a cone-beam of x-rays as in the first embodiment, the imaging region (effective field of view) is of cylindrical shape of radius o) centered on the axis of revolution. Reconstruction processing unit 12 defines a plurality of voxels (three-dimensional pixels) in this imaging region, and finds the backprojection data for each voxel. The three-dimensional image data or tomographic image data compiled by using this backprojection data is sent to display device 14, where it is displayed visually as a three-dimensional image or tomographic image.

For the purposes of this description we shall define an image to be a representation of a physical scene, in which the image has been generated by some imaging technology. Examples of imaging technology could include television or CCD cameras or X-ray, sonar or ultrasound imaging devices. The initial medium on which an image is recorded could be an electronic solid-state device, a photographic film, or some other device such as a photostimulable phosphor. That recorded image could then be converted into digital form by a combination of electronic (as in the case of a CCD signal) or mechanical/optical means (as in the case of digitizing a photographic film or digitizing the data from a photostimulable phosphor).

All embodiments of the present invention conveniently may be implemented using a conventional general purpose computer or micro-processor programmed according to the teachings of the present invention, as will be apparent to those skilled in the computer art. Appropriate software may readily be prepared by programmers of ordinary skill based on the teachings of the present disclosure, as will be apparent to those skilled in the software art. In particular, the computer housing may house a motherboard that contains a CPU, memory (e.g., DRAM, ROM, EPROM, EEPROM, SRAM, SDRAM, and Flash RAM), and other optional special purpose logic devices (e.g., ASICS) or configurable logic devices (e.g., GAL and reprogrammable FPGA). The computer also includes plural input devices, (e.g., keyboard and mouse), and a display card for controlling a monitor. Additionally, the computer may include a floppy disk drive; other removable media devices (e.g. compact disc, tape, and removable magneto-optical media); and a hard disk or other fixed high density media drives, connected using an appropriate device bus (e.g., a SCSI bus, an Enhanced IDE bus, or an Ultra DMA bus). The computer may also include a compact disc reader, a compact disc reader/writer unit, or a compact disc jukebox, which may be connected to the same device bus or to another device bus.

Examples of computer readable media associated with the present invention include compact discs, hard disks, floppy disks, tape, magneto-optical disks, PROMs (e.g., EPROM, EEPROM, Flash EPROM), DRAM, SRAM, SDRAM, etc. Stored on any one or on a combination of these computer readable media, the present invention includes software for controlling both the hardware of the computer and for enabling the computer to interact with a human user. Such software may include, but is not limited to, device drivers, operating systems and user applications, such as development tools. Computer program products of the present invention include any computer readable medium which stores computer program instructions (e.g., computer code devices) which when executed by a computer causes the computer to perform the method of the present invention. The computer code devices of the present invention may be any interpretable or executable code mechanism, including but not limited to, scripts, interpreters, dynamic link libraries, Java classes, and complete executable programs. Moreover, parts of the processing of the present invention may be distributed (e.g., between (1) multiple CPUs or (2) at least one CPU and at least one configurable logic device) for better performance, reliability, and/or cost. For example, an outline or image may be selected on a first computer and sent to a second computer for remote diagnosis.

The invention may also be implemented by the preparation of application specific integrated circuits or by interconnecting an appropriate network of conventional component circuits, as will be readily apparent to those skilled in the art.

The source of image data to the present invention may be any appropriate image acquisition device such as an X-ray machine or CT apparatus. Further, the acquired data may be digitized if not already in digital form. Alternatively, the source of image data being obtained and processed may be a memory storing data produced by an image acquisition device, and the memory may be local or remote, in which case a data communication network, such as PACS (Picture Archiving Computer System), may be used to access the image data for processing according to the present invention.

Numerous modifications and variations of the present invention are possible in light of the above teachings. It is therefore to be understood that within the scope of the appended claims, the invention may be practiced otherwise than as specifically described.

The invention claimed is:

1. A method of determining an image data value at a point of reconstruction in a computed tomography (CT) image of a scanned object, comprising:
   obtaining projection data of the scanned object;
   filtering the obtained projection data with both a one-dimensional ramp filter and a Hilbert filter to generate filtered data;
   applying a backprojection operator with inverse distance weighting to said filtered data to generate the image data value at the point of reconstruction in the CT image; and
   displaying the generated image data value, wherein the filtering step comprises
      applying projection subtraction to the obtained projection data to generate subtracted data;
      applying the Hilbert filter to the subtracted data to generate Hilbert-filtered data; and
      applying projection addition to the Hilbert-filtered data and ramp-filtered data to generate the filtered data, the ramp-filtered data being generated by filtering the obtained projection data with the one-dimensional ramp filter, and
   wherein the step of obtaining projection data produces two-dimensional projections and the step of applying the backprojection operator is applied only to said filtered data contained within a Tam window.

2. The method of claim 1, further comprising:
   repeating said applying step for a plurality of points of reconstruction in the CT image to obtain a plurality of image data values; and
   generating the CT image by arranging said plurality of image data values according to said plurality of points of reconstruction.

3. The method of claim 1, further comprising:
   repeating the step of applying the backprojection operator for a plurality of points of reconstruction in a volume of interest to obtain a plurality of image data values; and
   generating a CT volume by arranging said plurality of image data values according to said plurality of points of reconstruction in the volume of interest.

4. The method of claim 1, wherein the filtering step comprises:
   filtering said projection data with a modified ramp filter.

5. The method of claim 1, wherein the filtering step comprises:
   filtering said projection data with a modified ramp filter with an offset.

6. The method of claim 1, wherein the obtaining step comprises:
   obtaining the projection data using a CT system having one of a circular source trajectory, a helical source trajectory, and a saddle source trajectory.

7. The method of claim 1, wherein the filtering step comprises:
   filtering the obtained projection data using one of (1) horizontal filtering, (2) tangential filtering, (3) rotated filtering, and (4) Katsevich filtering.

8. The method of claim 1, wherein the obtaining step comprises:
   obtaining the projection data using a projection range that satisfies $\Lambda \geq \pi + 2 \arcsin(r_{FOV}/R)$, wherein $\Lambda$ is the projection range, $r_{FOV}$ is a radial measurement of a field of view (FOV), and R is a radial measurement of a source trajectory.

9. A method of determining an image data value at a point of reconstruction in a computed tomography (CT) image of a scanned object, comprising:
   obtaining projection data of the scanned object;
   filtering the obtained projection data with both a one-dimensional ramp filter and a Hilbert filter to generate filtered data;
   applying a backprojection operator with inverse distance weighting to said filtered data to generate the image data value at the point of reconstruction in the CT image; and
   displaying the generated image data value, wherein the filtering step comprises
      applying projection subtraction to the obtained projection data to generate subtracted data;
      applying the Hilbert filter to the subtracted data to generate Hilbert-filtered data; and
      applying projection addition to the Hubert-filtered data and ramp-filtered data to generate the filtered data, the ramp-filtered data being generated by filtering the obtained projection data with the one-dimensional ramp filter, the method further comprising
   applying redundancy weighting to said filtered data to generate weighted data, wherein the step of applying the backprojection operator is applied to said weighted data to generate the image data value at the point of reconstruction in the CT image.

10. The method of claim 9, further comprising:
repeating said step of applying the backprojection operator for a plurality of points of reconstruction in a region of interest within a same horizontal plane as the point of reconstruction to obtain a plurality of image data values; and
generating the CT image by arranging said plurality of image data values according to said plurality of points of reconstruction.

11. The method of claim 10, further comprising:
repeating said steps of (1) applying redundancy weighting, and (2) repeating said step of applying the backprojection operator for a plurality of points of reconstruction in a region of interest within a same horizontal plane, for a plurality of horizontal planes defined by a corresponding plurality of z-coordinates to generate a plurality of reconstructed image slices; and
generating a CT volume by arranging said plurality of reconstructed image slices according to the corresponding z-coordinates.

12. The method of claim 9, further comprising:
repeating the steps of applying redundancy weighting and applying the backprojection operator for a plurality of points of reconstruction in the CT image; and
generating the CT image by arranging said plurality of image data values according to said plurality of points of reconstruction.

13. The method of claim 9, wherein the step of applying a Hubert filter comprises:
applying a modified Hilbert filter to said subtracted data.

14. The method of claim 9, wherein the step of applying redundancy weighting comprises:
applying one of (1) Parker weighting, (2) generalized Parker (MHS) weighting, (3) over-scan (OS) weighting, (4) Noo weighting, (5) quasi cone-beam (Q3D) weighting, and (6) Tam window weighting to said filtered data.

15. The method of claim 9, wherein the step of applying a Hilbert filter comprises:
applying one of (1) horizontal filtering, (2) tangential filtering, (3) rotated filtering, and (4) Katsevich filtering to the subtracted data.

16. A system for determining an image data value at a point of reconstruction in a computed tomography (CT) image of a scanned object, comprising:
a CT scanning unit configured to generate projection data of the scanned object, the CT scanning unit including an X-ray source configured to generate X-rays and a detector having detector elements configured to produce the projection data of the scanned object; and
a processor, including:
a filtering unit configured to apply a ramp filter and a Hilbert filter to the projection data generated by the CT scanning unit to generate filtered data; and
a backprojecting unit configured to apply a backprojection operator with inverse distance weight to the filtered data generated by the filtering unit to generate the image data value at the point of reconstruction,
wherein the processor further comprises:
a projection subtraction unit configured to apply projection subtraction to the projection data generated by the CT scanning unit to generate subtracted data;
a Hilbert filtering unit configured to apply the Hilbert filter to the subtracted data generated by the projection subtraction unit to generate Hilbert-filtered data;

a projection addition unit configured to apply projection addition to (1) the Hilbert-filtered data generated by the Hilbert-filtering unit, and (2) ramp-filtered data generated by the filtering unit, to generate the filtered data; and
a weighting unit configured to apply redundancy weighting to the filtered data generated by the projection addition unit to generate weighted data,
wherein the backprojecting unit is configured to apply a backprojection operator with inverse distance weight to the weighted data generated by the weighting unit.

17. The system of claim 16, wherein the CT scanning unit is configured to produce two-dimensional projections and the backprojecting unit is configured to apply the backprojection operator only to said filtered data contained within a Tam window.

18. The system of claim 16, wherein the Hilbert filtering unit is configured to apply a
modified Hubert filter to the subtracted data generated by the projection subtraction unit.

19. The system of claim 16, wherein the weighting unit is configured to apply one of (1) Parker weighting, (2) generalized Parker (MHS) weighting, (3) over-scan (OS) weighting, (4) Noo weighting, (5) quasi cone-beam (Q3D) weighting, and (6) Tam window weighting to the filtered data generated by the projection addition unit.

20. The system of claim 16, wherein the filtering unit is configured to apply a modified ramp filter to the projection data generated by the CT scanning unit.

21. The system of claim 16, wherein the filtering unit is configured to apply a modified ramp filter with an offset to the projection data generated by the CT scanning unit.

22. The system of claim 16, wherein the CT scanning unit is configured to generate
projection data using one of a circular source trajectory, a helical source trajectory, and a saddle trajectory.

23. The system of claim 16, wherein the scanning unit is configured to generate the projection data using a reconstruction range that satisfies $\Lambda \geq \pi + 2 \arcsin(r_{FOV}/R)$, wherein $\Lambda$ is the projection range, $r_{FOV}$ is a radial measurement of a field of view (FOV), and R is a radial measurement of a source trajectory.

24. A computer-readable medium having embedded therein a computer program product that includes instructions for execution on a computer system, which when executed by the computer system, causes the computer system to determine an image data value at a point of reconstruction in a computed tomography (CT) image of a scanned object by performing the steps of:
obtaining projection data of the scanned object;
filtering the obtained projection data with both a one-dimensional ramp filter and a Hilbert filter to generate filtered data;
applying a backprojection operator with inverse distance weighting to said filtered data to generate the image data value at the point of reconstruction in the CT image; and
displaying the generated image data value, wherein the filtering step comprises
applying projection subtraction to the obtained projection data to generate subtracted data;
applying the Hilbert filter to the subtracted data to generate Hilbert-filtered data; and
applying projection addition to the Hilbert-filtered data and ramp-filtered data to generate the filtered data, the ramp-filtered data being generated by filtering the obtained projection data with the one-dimensional ramp filter, and wherein the step of obtaining projection data produces two-dimensional projections and the step of applying the backprojection operator is applied only to said filtered data contained within a Tam window.

25. The computer-readable medium of claim 24, the computer program product further comprising:
repeating said applying step for a plurality of points of reconstruction in a medical image to obtain a corresponding plurality of image data values; and
generating the CT image by arranging said plurality of image data values according to said plurality of points of reconstruction.

26. The computer-readable medium of claim 24, the computer program product further comprising:
repeating the step of applying the backprojection operator for a plurality of points of reconstruction in a volume of interest to obtain a plurality of image data values; and
generating a CT volume by arranging said plurality of image data values according to said plurality of points of reconstruction in the volume of interest.

27. The computer-readable medium of claim 24, wherein the filtering step comprises:
filtering said projection data with a modified ramp filter.

28. The computer-readable medium claim 24, wherein the filtering step comprises:
filtering said projection data with a modified ramp filter with an offset.

29. The computer-readable medium of claim 24, wherein the obtaining step comprises:
obtaining the projection data using a CT system having one of a circular source trajectory, a helical source trajectory, and a saddle source trajectory.

30. The computer-readable medium of claim 24, wherein the filtering step comprises:
filtering the obtained projection data using one of (1) horizontal filtering, (2) tangential filtering, (3) rotated filtering, and (4) Katsevich filtering.

31. The computer-readable medium of claim 24, wherein the obtaining step comprises:
obtaining the projection data using a reconstruction range that satisfies $\Lambda \geq \pi + 2 \arcsin(r_{FOV}/R)$, wherein $\Lambda$ is the projection range, $r_{FOV}$ is a radial measurement of a field of view (FOV), and R is a radial measurement of a source trajectory.

32. A computer-readable medium having embedded therein a computer program product that includes instructions for execution on a computer system, which when executed by the computer system, causes the computer system to determine an image data value at a point of reconstruction in a computed tomography (CT) image of a scanned object by performing the steps of:
obtaining projection data of the scanned object;
filtering the obtained projection data with both a one-dimensional ramp filter and a Hilbert filter to generate filtered data;
applying a backprojection operator with inverse distance weighting to said filtered data to generate the image data value at the point of reconstruction in the CT image;
displaying the generated image data value, wherein the filtering step comprises
applying projection subtraction to the obtained projection data to generate subtracted data;
applying the Hilbert filter to the subtracted data to generate Hilbert-filtered data; and
applying projection addition to the Hilbert-filtered data and ramp-filtered data to generate the filtered data, the ramp-filtered data being generated by filtering the obtained projection data with the one-dimensional ramp filter, the steps further including
applying redundancy weighting to said filtered data to generate weighted data, wherein the step of applying the backprojection operator is applied to said weighted data to generate the image data value at the point of reconstruction in the CT image.

33. The computer-readable medium of claim 32, the computer program product further comprising:
repeating said step of applying the backprojection operator for a plurality of points of reconstruction in a region of interest within a same horizontal plane as the point of reconstruction to obtain a plurality of image data values; and
generating the CT image by arranging said plurality of image data values according to said plurality of points of reconstruction.

34. The computer-readable medium of claim 33, the computer program product further comprising:
repeating said steps of (1) applying redundancy weighting, and (2) repeating said step of applying the backprojection operator for a plurality of points of reconstruction in a region of interest within a same horizontal plane, for a plurality of horizontal planes defined by a corresponding plurality of z-coordinates to generate a plurality of reconstructed image slices; and
generating a CT volume by arranging said plurality of reconstructed image slices according to the corresponding z-coordinates.

35. The computer-readable medium of claim 32, the computer program product further comprising:
repeating the steps of applying redundancy weighting and applying the backprojection operator for a plurality of points of reconstruction in the CT image; and
generating the CT image by arranging said plurality of image data values according to said plurality of points of reconstruction.

36. The computer-readable medium of claim 32, wherein the step of applying a Hilbert filter comprises:
applying a modified Hilbert filter to said subtracted data.

37. The computer-readable medium product of claim 32, wherein the step of applying redundancy weighting comprises:
applying one of (1) Parker weighting, (2) generalized Parker (MHS) weighting, (3) over-scan (OS) weighting, (4) Noo weighting, (5) quasi cone-beam (Q3D) weighting, and (6) Tam window weighting to said filtering data.

38. The computer-readable medium of claim 32, wherein the step of applying a Hilbert filter comprises:
applying one of (1) horizontal filtering, (2) tangential filtering, (3) rotated filtering, and (4) Katsevich filtering to the subtracted data.

* * * * *